United States Patent
Elsayed et al.

(10) Patent No.: US 11,143,592 B2
(45) Date of Patent: Oct. 12, 2021

(54) METHOD OF DETECTING ANTIMONY IONS AND METHOD OF REMOVING ANTIMONY IONS USING A FLUORESCENT NANOCOMPOSITE

(71) Applicant: King Abdulaziz University, Jeddah (SA)

(72) Inventors: Waleed Elsayed Mahmoud Elsayed, Jeddah (SA); Ahmed Abdullah Salem Al-Ghamdi, Jeddah (SA); Yusuf Abdulaziz Al-Turki, Jeddah (SA)

(73) Assignee: King Abdulaziz University, Jeddah (SA)

( * ) Notice: Subject to any disclaimer, the term of this patent is extended or adjusted under 35 U.S.C. 154(b) by 127 days.

(21) Appl. No.: 16/549,526

(22) Filed: Aug. 23, 2019

(65) Prior Publication Data
US 2021/0054269 A1 Feb. 25, 2021

(51) Int. Cl.
*G01N 33/18* (2006.01)
*G01N 21/64* (2006.01)
(Continued)

(52) U.S. Cl.
CPC ........ *G01N 21/643* (2013.01); *B01J 20/0207* (2013.01); *B01J 20/0248* (2013.01);
(Continued)

(58) Field of Classification Search
CPC .... G01N 31/22; G01N 33/1813; B82Y 15/00; C02F 1/288; C02F 2101/20; B01J 20/0248
See application file for complete search history.

(56) References Cited

U.S. PATENT DOCUMENTS

| | | | | |
|---|---|---|---|---|
| 10,823,674 B1 * | 11/2020 | Elsayed | ............... | B01J 20/0207 |
| 2013/0226268 A1 | 8/2013 | Pan | | |

FOREIGN PATENT DOCUMENTS

| | | |
|---|---|---|
| CN | 108929692 A | 12/2018 |
| DE | 2 214 226 A1 | 10/1973 |

(Continued)

OTHER PUBLICATIONS

Manvendra Kumar, et al., "Europium activated gadolinium sulfide nanoparticles", RSC Advances, Issue 110. 2016, pp. 108523-108529 (Abstract only).
(Continued)

*Primary Examiner* — Christopher Adam Hixson
*Assistant Examiner* — Michelle Adams
(74) *Attorney, Agent, or Firm* — Oblon, McClelland, Maier & Neustadt, L.L.P.

(57) ABSTRACT

A fluorescent nanocomposite which includes a thallium doped gadolinium chalcogenide having formula $Tl_xGd_{1-x}Y$, wherein x is 0.01 to 0.1, and Y is selected from the group consisting of S, Se, or Te, and a benzothiazolium salt bound to a surface of the thallium doped gadolinium chalcogenide. A method of detecting antimony ions in a fluid sample whereby the fluid sample is contacted with the fluorescent nanocomposite to form a mixture, and a fluorescence emission profile of the mixture is measured to determine a presence or absence of antimony ions in the fluid sample, wherein a reduction in intensity of a fluorescence emissions peak associated with the fluorescent nanocomposite indicates the presence of antimony ions in the fluid sample.

9 Claims, 5 Drawing Sheets

(51) Int. Cl.

| | | |
|---|---|---|
| *G01N 31/22* | (2006.01) | |
| *C02F 1/28* | (2006.01) | |
| *C09K 11/62* | (2006.01) | |
| *C09K 11/07* | (2006.01) | |
| *B01J 20/02* | (2006.01) | |
| *C09K 11/08* | (2006.01) | |
| *C09K 11/56* | (2006.01) | |
| *C09K 11/77* | (2006.01) | |
| *B82Y 40/00* | (2011.01) | |
| *B82Y 15/00* | (2011.01) | |
| *C02F 101/20* | (2006.01) | |
| *B82Y 30/00* | (2011.01) | |
| *G01N 21/17* | (2006.01) | |
| *B82Y 20/00* | (2011.01) | |

(52) U.S. Cl.
CPC ........... *B01J 20/0266* (2013.01); *C02F 1/288* (2013.01); *C09K 11/07* (2013.01); *C09K 11/0805* (2013.01); *C09K 11/0822* (2013.01); *C09K 11/562* (2013.01); *C09K 11/621* (2013.01); *C09K 11/7701* (2013.01); *G01N 21/6428* (2013.01); *G01N 31/22* (2013.01); *G01N 33/1813* (2013.01); *B82Y 15/00* (2013.01); *B82Y 20/00* (2013.01); *B82Y 30/00* (2013.01); *B82Y 40/00* (2013.01); *C02F 2101/20* (2013.01); *G01N 2021/174* (2013.01); *G01N 2021/6432* (2013.01)

(56) References Cited

FOREIGN PATENT DOCUMENTS

| | | |
|---|---|---|
| JP | 2001-305030 A | 10/2001 |
| JP | 2003-241101 A | 8/2003 |
| KR | 10-1223671 B1 | 1/2013 |
| WO | WO 2016/022012 A1 | 2/2016 |

OTHER PUBLICATIONS

R. Gautam, et al., "First Principle Investigations on Electronic, Magnetic, Thermodynamic, and Transport Properties of $TlGdX_2$ (X = S, Se, Te)", Acta Physica Polonica A, vol. 132, No. 4, 2017, pp. 1371-1378.

Aleksey Vasilev, et al., "Novel environmentally benign procedures for the synthesis of styryl dyes", Dyes and Pigments, vol. 77, 2008, pp. 550-555.

Shirish Paranjpe, "Synthesis of Novel Fluorescent Benzothiazole Cyanine Dyes as Potential Imaging Agents", Chemistry Thesis, Department of Chemistry, Scholarworks@Georgia State University, Dec. 18, 2012, 153 pages.

\* cited by examiner

METHOD OF DETECTING ANTIMONY IONS AND METHOD OF REMOVING ANTIMONY IONS USING A FLUORESCENT NANOCOMPOSITE

BACKGROUND OF THE INVENTION

Field of the Invention

The present invention relates to an antimony selective fluorescent chemosensor, particularly a fluorescent nanocomposite of a thallium doped gadolinium chalcogenide and a benzothiazolium salt, and methods of detecting antimony ions in a fluid sample with the fluorescent nanocomposite.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Antimony is a semi-metallic element that has two different forms either in silvery metallic form or nonmetallic grey powder form. It is mainly used in semiconducting devices such as infrared detectors, diodes, cable sheathing and batteries. Additionally, various compounds based on antimony have been developed for the synthesis of ceramic enamels, paints and flame-proofing materials. Antimony also exists in water and soil, and causes water and soil pollution. Exposure to antimony causes harmful diseases such as diarrhea, heart problems, lung diseases, stomach ulcers, reproductive failure, cancer and severe vomiting. Therefore, the maximum permissible amount of antimony should not exceed 9 mg/L according to the world health organization (WHO). Because of the toxicity of antimony, there is a real demand to develop an efficient technique to monitor the amount of antimony in water. Various approaches have been developed to determine the amount of antimony such as electrochemical techniques, atomic emission spectrometry, stripping chronopotentiometric (SCP) methods, and inductive coupled plasma spectrometry. While these approaches can be successfully used to detect antimony, their accuracy diminishes in the presence of other elements. Further, such approaches suffer from a high cost (particularly the cost of specialized equipment), tedious preparation of samples, difficult operation, and the need for trained professionals to carry out the analysis. Thus such methods are not practical. Another strategy for detection of antimony involves luminescence techniques. However, such techniques are troubled by photobleaching, high temperature instability, and sludge generation.

In view of the forgoing, there is a need for effective, sensitive, and selective fluorescent chemosensors for the detection of antimony, which are easy and inexpensive to make, and which are can operate under a broad range of pH values and temperatures.

SUMMARY OF THE INVENTION

Accordingly, it is one object of the present invention to provide a fluorescent nanocomposite of a thallium doped gadolinium chalcogenide and a benzothiazolium salt for the detection of antimony ions, which is highly sensitive to and selective for only antimony ions, is easy to make, and which can operate under a broad range of pH values and temperatures.

It is another object of the present disclosure to provide methods for the detection of antimony and/or determination of antimony ion concentration in a fluid sample using the fluorescent nanocomposite.

It is another object of the present disclosure to provide methods for removing antimony ions from a fluid sample using the fluorescent nanocomposite as an adsorbent.

Thus the present disclosure provides:

A fluorescent nanocomposite that contains (i) a thallium doped gadolinium chalcogenide having formula $Tl_xGd_{1-x}Y$, wherein x is 0.01 to 0.1, and Y is selected from the group consisting of S, Se, or Te, and (ii) a benzothiazolium salt of formula I bound to a surface of the thallium doped gadolinium chalcogenide,

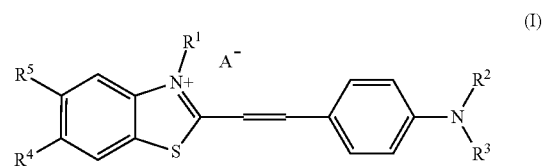

(I)

wherein:
$R^1$ is a $C_1$-$C_4$ alkyl or an arylalkyl,
$R^2$ and $R^3$ are independently an optionally substituted alkyl group, or wherein $R^2$ and $R^3$ together form a five or six membered ring with the nitrogen to which they are attached,
$R^4$ and $R^5$ are independently a hydrogen or an alkyl group, and
A is Br, I, or $ClO_4$.

In some embodiments, x is 0.04 to 0.06 and Y is S.
In some embodiments, the thallium doped gadolinium chalcogenide is $Tl_{0.05}Gd_{0.95}S$.
In some embodiments, the thallium doped gadolinium chalcogenide is in the form of core-type quantum dots having an average particle size of 3 to 7 nm.
In some embodiments, the thallium doped gadolinium chalcogenide is present in an amount of 14 to 35 wt. %, based on a total weight of the fluorescent nanocomposite.
In some embodiments, $R^1$ is a methyl, ethyl, or benzyl; $R^2$ and $R^3$ are independently a methyl, an ethyl, or a 2-cyanoethyl; and $R^4$ and $R^5$ are independently a hydrogen or a methyl.
In some embodiments, the benzothiazolium salt of formula I is

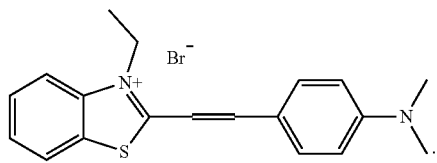 [SMILES: CC[n+]1c(C=Cc2ccc(N(C)C)cc2)sc2ccccc21 ; [Br-]]

In some embodiments, a weight ratio of the benzothiazolium salt of formula I to the thallium doped gadolinium chalcogenide is 1.95:1 to 6.0:1.
In some embodiments, the benzothiazolium salt of formula I is present in an amount of 65 to 86 wt. %, based on a total weight of the fluorescent nanocomposite.

In some embodiments, the fluorescent nanocomposite consists of the thallium doped gadolinium chalcogenide and the benzothiazolium salt of formula I.

In some embodiments, the fluorescent nanocomposite has a fluorescence emissions peak at 605 to 620 nm at an excitation wavelength of 450 nm.

A method of detecting antimony ions in a fluid sample that includes contacting the fluid sample with the fluorescent nanocomposite to form a mixture, and measuring a fluorescence emission profile of the mixture to determine a presence or absence of antimony ions in the fluid sample, wherein a reduction in intensity of a fluorescence emissions peak associated with the fluorescent nanocomposite indicates the presence of antimony ions in the fluid sample.

In some embodiments, 0.5 to 10 mg of the fluorescent nanocomposite is employed per 1 mL of the fluid sample during the contacting.

In some embodiments, the mixture has a pH of 2 to 11 and a temperature of 10 to 70° C.

In some embodiments, antimony ions are present in the fluid sample, and wherein a concentration of antimony ions in the fluid sample is from 0.0001 to 1,000 mg/L.

In some embodiments, the fluid sample is a wastewater, a tap water, a well water, or a river water.

In some embodiments, the method further comprises determining a concentration of the antimony ions in the fluid sample by measuring a relative intensity of the mixture $(I_0/I)$, defined as a ratio of a maximum fluorescence intensity of the fluorescent nanocomposite in a blank sample devoid of antimony ions $(I_0)$ to a maximum fluorescence intensity of the mixture (I), and comparing to a calibration curve that relates antimony ion concentration to relative intensity $(I_0/I)$.

In some embodiments, the fluid sample comprises one or more cations of potassium, magnesium, iron, arsenic, cobalt, cadmium, mercury, aluminum, and chromium, and the method is selective for detection of antimony ions, wherein only the presence of antimony ions in the mixture produces a reduction in the intensity of the fluorescence emissions peak of greater than 2%.

In some embodiments, the method has a antimony ion detection lower limit of 0.00001 to 0.0001 mg/L.

A method of removing antimony ions from a fluid sample that includes contacting the fluid sample with the fluorescent nanocomposite to form a mixture, whereby antimony ions adsorb onto the fluorescent nanocomposite to form a loaded nanocomposite, and separating the loaded nanocomposite from the mixture by centrifugation and/or filtration, wherein a concentration of antimony ions in the fluid sample after the contacting and separating is lower than an initial concentration of antimony ions in the fluid sample.

BRIEF DESCRIPTION OF THE DRAWINGS

The foregoing paragraphs have been provided by way of general introduction, and are not intended to limit the scope of the following claims. A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1:
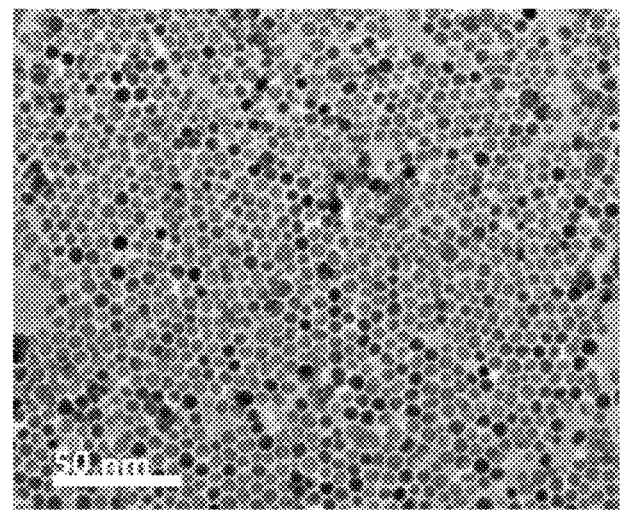
FIG. 1 illustrates a SEM image for the prepared $Tl_{0.05}Gd_{0.95}S$ nanoparticles.

In the following description, it is understood that other embodiments may be utilized and structural and operational changes may be made without departure from the scope of the present embodiments disclosed herein.

Definitions

As used herein, "wastewater" means a water source obtained from storm drains, sedimentation ponds, runoff/outflow, landfills, as well as water sources resulting/obtained from industrial processes such as factories, mills, farms, mines, quarries, industrial drilling operations, oil and gas recovery operations, pharmaceutical processes, papermaking processes, food preparation processes, phase separation processes, washing processes, waste treatment plants, toilet processes, power stations, incinerators, spraying and painting, navigation processes, aviation processes, automotive plants, fuel cell manufacturing operations, or any other manufacturing or commercial enterprise, which comprises water and one or more compounds or materials derived from such industrial processes, including partially treated water from these sources.

As used herein, the term "fatty" describes a compound with a long-chain (linear) hydrophobic portion made up of hydrogen and anywhere from 6 to 26, 8 to 24, 10 to 22, 12 to 20, 14 to 18 carbon atoms, which may be fully saturated or partially unsaturated, and optionally attached to a polar functional group such as a hydroxyl group, an amine group, or a carboxyl group (e.g., carboxylic acid). Fatty alcohols, fatty amines, fatty acids, fatty esters, and fatty amides are examples of materials which contain a fatty portion, and are thus considered "fatty" compounds herein.

As used herein, "alkoxylated" or "alkoxylate" refers to compounds containing a (poly)ether group (i.e., (poly)oxyalkylene group) derived from reaction with, oligomerization of, or polymerization of one or more alkylene oxides having 2 to 4 carbon atoms, and specifically includes (poly)oxyethylene (derived from ethylene oxide, EO), (poly)oxypropylene (derived from propylene oxide, PO), and (poly)oxybutylene (derived from butylene oxide, BO), as well as mixtures thereof.

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, aliphatic fragment having 1 to 26 carbon atoms, preferably 2 to 24, preferably 3 to 22, preferably 4 to 20, preferably 5 to 18, preferably 6 to 16, preferably 7 to 14, preferably 8 to 12, preferably 9 to 10. Non-limiting examples include, but are not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, lauryl, myristyl, cetyl, stearyl, and the like, including guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), and cycloalkyl groups such as cyclopropyl, cyclobutyl, cyclopentyl, cyclohexyl, norbornyl, and adamantyl. The term "lower alkyl" is used herein to describe alkyl groups having 1 to 5 carbon atoms (e.g., methyl, ethyl, n-propyl, etc.).

As used herein, unless otherwise specified, the term "aryl" refers to an aromatic group containing only carbon in the aromatic ring(s), such as phenyl, biphenyl, naphthyl, anthracenyl, and the like. The term "heteroarene" refers to an arene compound or aryl group where at least one carbon atom is replaced with a heteroatom (e.g., nitrogen, oxygen, sulfur) and includes, but is not limited to, pyridine, pyrimidine, quinoline, isoquinoline, pyrazine, pyridazine, indole, pyrrole, oxazole, furan, benzofuran, thiophene, benzothiophene, isoxazole, pyrazole, triazole, tetrazole, indazole, purine, carbazole, imidazole, and benzimidazole.

The term "arylalkyl" refers to a straight or branched chain alkyl moiety having 1 to 26 carbon atoms that is substituted by an aryl group as defined above, and includes, but is not limited to, benzyl, 2-phenethyl, and 2-phenylpropyl.

As used herein, "optionally substituted" means that at least one hydrogen atom is replaced with a non-hydrogen group, provided that normal valencies are maintained and that the substitution results in a stable compound. Such optional substituents may be selected from aryl, alkoxy, aryloxy, arylalkyloxy, carboxy, hydroxy, halo (e.g. chlorine, bromine, fluorine or iodine), amino (e.g. alkylamino, arylamino, arylalkylamino, alkanoylamino, either mono- or disubstituted), oxo, and the like.

As used herein, the term "chalcogenide" refers to a chemical compound containing at least one electropositive element and at least one chalcogen anion selected from the group consisting of a sulfide, a selenide, a telluride, and a polonide. Thus, chalcogenides differ from oxides in the present disclosure.

Fluorescent Nanocomposite

The present disclosure provides a fluorescent nanocomposite (chemosensor) for the sensitive and selective detection of antimony ions (e.g., $Sb^{5+}$) in a fluid sample, including those fluid samples which contain a host of different cations. The fluorescent nanocomposite disclosed herein is easy to manufacture, including on-scale manufacture, and is remarkably photostable under a wide range of pH, temperature, and storage time conditions. It has been found that the fluorescent nanocomposite of the present disclosure, upon interaction/adsorption with antimony ions, produces a fluorescence emission peak of reduced intensity, but remains unchanged when in the presence of other common cations. This characteristic allows for extremely easy detection and/or quantification of antimony ions.

The present disclosure thus provides a fluorescent nanocomposite comprising, consisting of, or consisting essentially of a thallium doped gadolinium chalcogenide and a benzothiazolium salt bound to a surface of the thallium doped gadolinium chalcogenide.

Thallium Doped Gadolinium Chalcogenide

The fluorescent nanocomposite of the present disclosure contains a metal chalcogenide, preferably a transition metal chalcogenide (including inner transition metal chalcogenide) or a post-transition metal chalcogenide. In preferred embodiments, the fluorescent nanocomposite of the present disclosure contains a doped transition metal chalcogenide, preferably a transition metal chalcogenide that is doped with a post-transition metal. In some embodiments, the metal chalcogenide is a metal monochalcogenide.

In preferred embodiments, the chalcogenide is a thallium doped gadolinium chalcogenide having formula $Tl_xGd_{1-x}Y$. Here, the sub-numerals of thallium (Tl) and gadolinium (Gd) correspond to a molar fraction of Tl and Gd elements present in the crystal structure of the chalcogenide, where the total number of moles of Tl and Gd is equal to the number of moles of the chalcogen anion (i.e., when the number of moles of chalcogen anion is 1, then the total number of moles of Tl+Gd is equal to 1). Preferably, the gadolinium metal is the predominant metal. While various thallium doped gadolinium chalcogenides may be provided herein, it is preferred that x is from 0.001 to 0.3, preferably 0.005 to 0.2, preferably 0.01 to 0.1, preferably 0.02 to 0.08, preferably 0.03 to 0.07, preferably 0.04 to 0.06, preferably 0.05 (when x=0.05, this corresponds to 5 mol % thallium and 95 mol % gadolinium).

Also in the above formula, Y represents the chalcogen anion. Y may be S, Se, or Te, preferably S or Se, preferably S. When Y is S, the thallium doped gadolinium chalcogenide may be referred to as thallium doped gadolinium sulfide. Similar to gadolinium sulfide (GdS), the thallium doped gadolinium sulfide of the present disclosure preferably has a cubic crystal lattice/structure, as determined by X-ray diffraction (XRD).

In preferred embodiments, the thallium doped gadolinium chalcogenide is $Tl_{0.05}Gd_{0.95}S$.

The thallium doped gadolinium chalcogenide may be present in the form of nanoparticles of various morphologies, for example three dimensional nanoparticles (which have all three dimensions of less than 100 nm) such as nanospheres, nanogranules and nanobeads, two-dimensional nanoparticles (which have two dimensions of less than 100 nm) such as nanosheets, nanoplatelets, nanolaminas and nanoshells, and one-dimensional nanoparticles (which have one dimension of less than 100 nm) such as nanorods, nanotubes, nanofibers and nanowhiskers. Preferably, the thallium doped gadolinium chalcogenide is in the form of spherical nanoparticles.

In some embodiments, the thallium doped gadolinium chalcogenide is in the form of quantum dots. Quantum dots are semiconductor particles typically a few nanometers in size, having optical and electronic properties that differ from larger particles. That is, when quantum dots are illuminated, some of the electrons receive enough energy to break free from the atoms and allows them to move around the nanoparticle, creating a conductance band in which electrons are free to move through a material and conduct electricity. When these electrons drop back into the outer orbit around the atom (the valence band) they emit light. The color of that light depends on the energy difference between the conductance band and the valence band.

In some embodiments, the fluorescent nanocomposite is formed from core-shell quantum dots or alloyed quantum dots made of the thallium doped gadolinium chalogenide described herein plus another chalcogenide material or quantum dot material including, but not limited to, CdTe, PbS, CdSe, ZnS, ZnSe, ZnTe, CdSeS, ZnS/ZnSe, PbSe, CdS, InAs, CdS/ZnS, CdSe/ZnS, CdSe/CdS, InAs/CdSe, BN, BP, BAs, AlN, AlP, AlAs, AlSb, GaN, GaP, GaSb, InN, InP, InAs, InSb, ZnO, HgS, HgSe, HgTe, MgTe, MgSe, C, Si, Ge, BeTe, AlGaAs, GaInP, GaInAs, AlGaInP, AlGaAsSb, InAsSbP, InGaN, ZnSSe, ZnCdSe, and PbSnSeTe, just to name a few. The thallium doped gadolinium chalogenide may form the core or the shell of such core-shell quantum dots.

In preferred embodiments, the fluorescent nanocomposite is formed from core-type quantum dots of thallium doped gadolinium chalcogenide, i.e., the quantum dots are single component materials with a uniform composition of the thallium doped gadolinium chalcogenide (e.g., $Tl_{0.05}Gd_{0.95}S$). In these embodiments, the thallium doped gadolinium chalcogenide is the only metal chalcogenide present in the fluorescent nanocomposite. In some embodiments, the fluorescent nanocomposite is substantially free of doped gadolinium chalcogenides other than the thallium doped gadolinium chalcogenide described herein, for example, the fluorescent nanocomposite may be devoid of GdS or $Gd_2S_3$ which are doped with Eu, La, Ce, Pr, Nd, Sm, Tb, Dy, Ho, Er, Tm, Yb, Lu, Sc, Y, among others. In preferred embodiments, the fluorescent nanocomposite contains no europium (Eu) (in metal or cation form).

In some embodiments, the fluorescent nanocomposite may optionally contain, but is preferably substantially free of, dichalcogenides, such as $TlGdY_2$ (where Y is S, Se, or Te).

In preferred embodiments, other than the thallium doped gadolinium chalcogenide described herein, the fluorescent nanocomposite of the present disclosure is substantially free of other quantum dots such as one or more of CdTe, PbS, CdSe, ZnS, ZnSe, ZnTe, CdSeS, ZnS/ZnSe, PbSe, CdS, CdS/ZnS, CdSe/ZnS, CdSe/CdS, InAs/CdSe, BN, BP, BAs, AlN, AlP, AlAs, AlSb, GaN, GaP, GaSb, InN, InP, InAs, InSb, ZnO, HgS, HgSe, HgTe, MgTe, MgSe, C, Si, Ge, BeTe, AlGaAs, GaInP, GaInAs, AlGaInP, AlGaAsSb, InAsSbP, InGaN, ZnSSe, ZnCdSe, and PbSnSeTe, for example those disclosed in US2013/0226268A1, JP2001305030A, and JP2003241101A, each incorporated herein by reference in its entirety.

The average particle size (diameter) of the thallium doped gadolinium chalcogenide quantum dots may vary, but typical values may range from 3 to 7 nm, preferably 3.5 to 6.5 nm, preferably 4 to 6 nm, preferably 4.5 to 5.5 nm, preferably 5 nm.

In some embodiments, the thallium doped gadolinium chalcogenide is present in the fluorescent nanocomposite in an amount of 14 to 35 wt. %, preferably 15 to 34 wt. %, preferably 17 to 32 wt. %, preferably 19 to 30 wt. %, preferably 21 to 28 wt. %, preferably 23 to 26 wt. %, preferably 25 wt. %, based on a total weight of the fluorescent nanocomposite.

The thallium doped gadolinium chalcogenide may be prepared using any procedure used for forming doped metal chalcogenides known to those of ordinary skill in the art. In one example, a polyol approach is utilized. Here, a gadolinium(III) salt and thallium(I) salt are dissolved in a polyol solvent in an appropriate ratio to provide the desired ratio of gadolinium to thallium in the final thallium doped gadolinium chalcogenide product. Typically, a weight ratio of the gadolinium(III) salt to the thallium(I) salt ranges from 20:1 to 70:1, preferably 30:1 to 68:1, preferably 40:1 to 64:1, preferably 50:1 to 62:1, preferably 55:1 to 60:1. A variety of gadolinium(III) salts may be used, with specific mention being made to tris(cyclopentadienyl)gadolinium, tris(N,N-bis(trimethylsilyl)amide)gadolinium(III), tris(tetramethylcyclopentadienyl)gadolinium(III), gadolinium(III) tris(isopropoxide), gadolinium(III) acetate, galdolinium(III) acetylacetonate, gadolinium(III) chloride, gadolinium(III) nitrate, and the like. Preferably tris(cyclopentadienyl)gadolinium is used as the gadolinium(III) salt. A variety thallium (I) salts may be used herein, with specific mention being made to thallium heptafluorobutyrate, thallium cyclohexanebutyrate, thallium pentafluoropropionate, thallium lactate, thallium p-toluenesulfonate, thallium tetrafluoroborate, and the like. Preferably, thallium pentafluoropropionate is used as the thallium(I) salt. The polyol solvent used in the polyol approach may include, but is not limited to, ethylene glycol (1,2-ethanediol), diethylene glycol, triethylene glycol, tetraethylene glycol, propylene glycol, dipropylene glycol, 1,3-propanediol, 1,3-butanediol, 1,4-butanediol, 1,6-hexanediol, glycerol, and pentaerythritol, preferably ethylene glycol is utilized.

The resulting mixture may be optionally heated, for example to a temperature of 40 to 100° C., preferably 50 to 98° C., preferably 60 to 96° C., preferably 70 to 94° C., preferably 80 to 92° C., preferably 90° C., and placed under an inert atmosphere such as argon or nitrogen, preferably nitrogen. Then, to this mixture, a sulfur source such as elemental sulfur, an aryl trifluoromethyl sulfide (e.g., phenyl (trifluoromethyl)sulfide), a N,N-disubstituted thiourea (e.g., (Z)-1-(octadec-9-enyl)-3-phenylthiourea), etc. may be added to provide a concentration of the sulfur source in the mixture of about 0.8 to 2 mM, preferably 0.9 to 1.9 mM, preferably 1 to 1.8 mM, preferably 1.1 to 1.7 mM, preferably 1.2 to 1.6 mM, preferably 1.3 to 1.5 mM. Then after addition of the sulfur source, the temperature of the entire mixture may be raised to 100 to 180° C., preferably 120 to 160° C., preferably 140 to 150° C., or at the reflux temperature of the polyol solvent, and kept at said elevated temperature with optional stirring/mixing/agitation for 15 to 120 minutes, preferably 30 to 100 minutes, preferably 45 to 90 minutes, preferably 60 to 75 minutes to provide a suspension. The resulting solids in the suspension may then be collected, for example via centrifugation at 10,000 to 20,000 rpm, preferably 12,000 to 18,000 rpm, preferably 14,000 to 16,000 rpm, and subsequently dried for example at 40 to 90° C., preferably 50 to 80° C., preferably 60 to 70° C., to afford the thallium doped gadolinium chalcogenide in the form of quantum dots.

Benzothiazolium Salt

The fluorescent nanocomposite of the present disclosure also includes a benzothiazolium salt bound to a surface of the thallium doped gadolinium chalcogenide. The benzothiazolium salt may be a 2-styryl-benzothiazolium salt, preferably a disubstituted 4-aminostyryl-benzothiazolium salt. In preferred embodiments, the benzothiazolium salt is of formula I

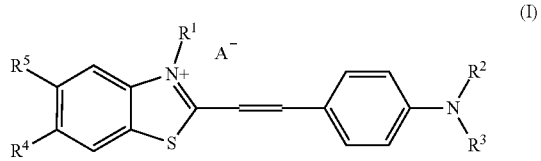

wherein:

$R^1$ is a $C_1$-$C_4$ alkyl or an arylalkyl, $R^2$ and $R^3$ are independently an optionally substituted alkyl group, or wherein $R^2$ and $R^3$ together form a five or six membered ring with the nitrogen to which they are attached, $R^4$ and $R^5$ are independently a hydrogen or an alkyl group, and A is Br, I, or $ClO_4$.

In some embodiments, $R^1$ is a $C_1$-$C_4$ alkyl, preferably a $C_1$-$C_3$ alkyl, preferably $C_1$-$C_2$ alkyl, such as methyl, ethyl, propyl, butyl. Preferably $R^1$ is methyl or ethyl, preferably ethyl. Alternatively, $R^1$ may be an arylalkyl such as benzyl, 2-phenethyl, 2-phenylpropyl, 3-phenylpropyl, and the like, preferably benzyl.

$R^2$ and $R^3$ are independently an optionally substituted alkyl group, preferably an optionally substituted $C_1$-$C_4$ alkyl, preferably an optionally substituted $C_1$-$C_3$ alkyl, preferably an optionally substituted $C_1$-$C_2$ alkyl, for example, a methyl, ethyl, propyl, butyl, trifluoromethyl, 2-cyanoethyl, 2-alkoxyethyl (e.g., 2-methoxyethyl), 2-hydroxyethyl, and the like. In some embodiments, $R^2$ and $R^3$ are the same optionally substituted alkyl group (e.g., $R^2$ and $R^3$ are both methyl). In some embodiments, $R^2$ and $R^3$ are different (e.g., $R^2$ is an ethyl group and $R^3$ is a 2-cyanoethyl group). In preferred embodiments, $R^2$ and $R^3$ are both methyl. Alternatively, $R^2$ and $R^3$ may together form a five or six membered ring with the nitrogen to which they are attached, i.e., $R^2$ and $R^3$ may be linked together thereby forming a 5- or a 6-membered heterocyclic ring including, but not limited to, a morpholinyl, a piperazinyl (e.g., N-methylpiperazinyl), a piperidinyl, and a pyrolidinyl, as shown below:

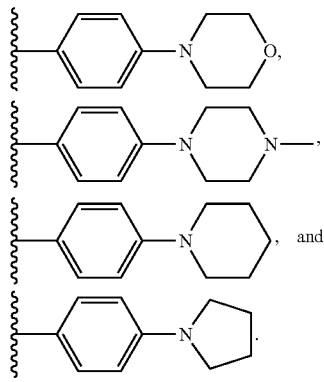

$R^4$ and $R^5$ may be independently a hydrogen or an alkyl group, preferably a $C_1$-$C_4$ alkyl, preferably a $C_1$-$C_3$ alkyl, $C_1$-$C_2$ alkyl, preferably a $C_1$ alkyl, for example, hydrogen, methyl, ethyl, propyl, butyl, preferably hydrogen and methyl. In some embodiments, $R^4$ and $R^5$ are the same. In some embodiments, $R^4$ and $R^5$ are different. In some embodiments, one of $R^4$ and $R^5$ is an alkyl group (e.g., methyl) while the other is hydrogen. In preferred embodiments, both $R^4$ and $R^5$ are hydrogen.

A may be Br, I, or $ClO_4$, preferably A is Br or I, preferably Br.

In preferred embodiments, the benzothiazolium salt of formula I is

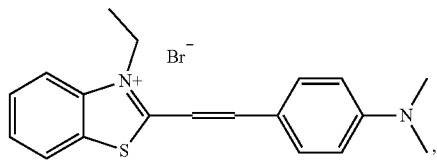 [SMILES: CC[n+]1c(C=Cc2ccc(N(C)C)cc2)sc2ccccc21 ; [Br-]]

(2-(4-(dimethylamino)styryl)-3-ethyl-benzothiazolium bromide).

The benzothiazolium salt of formula I may be commercially available or otherwise readily accessible by methods known to those of ordinary skill in the art, see for example, Vasilev, A. et al. "Novel environmentally benign procedures for the synthesis of styryl dyes" Dyes and Pigments, 2008, 77, 550-555, incorporated herein by reference in its entirety. For example, the benzothiazolium salt of formula I may be obtained through a condensation reaction between a 2-methylbenzothiazolium salt of formula II and a 4-aminobenzaldehyde of formula III,

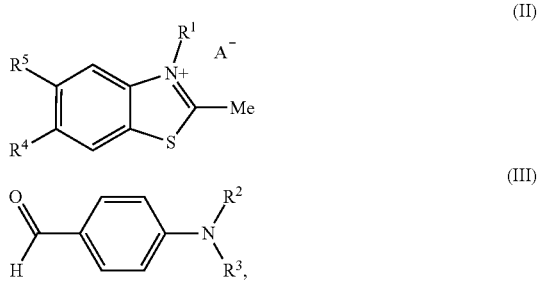

wherein $R^1$, $R^2$, $R^3$, $R^4$, $R^5$, and A are as defined previously. The condensation reaction may be performed using any procedures known to those of ordinary skill in the art, including, but not limited to, high temperature/organic solvent conditions and microwave conditions, preferably microwave under solvent-free conditions and using a known olefination catalyst such as sodium hydroxide, ammonium bicarbonate, sodium bicarbonate, sodium phosphate monobasic, para-toluene sulfonic acid, ammonium acetate, triphenylphosphine, potassium carbonate, and the like.

The 2-methylbenzothiazolium salt of formula II may be obtained via commercial sources or through known a quaternization reaction with an optionally substituted 2-methylbenzothiazole with an electrophile containing the $R^1$ group. Likewise, the 4-aminobenzaldehyde of formula III may be obtained from commercial sources, or may be synthesized, for example, using a Vilsmeier-Haack reaction of a suitably substituted aniline (Ph-$NR^2R^3$).

After the benzothiazolium salt of formula I has been provided, it may be used for decorating the surface of the thallium doped gadolinium chalcogenide to form the fluorescent nanocomposite. Surface decoration may be performed by dissolving the benzothiazolium salt of formula I in an appropriate solvent such as a monoalcohol solvent (e.g., methanol, ethanol, propanol, isopropanol, n-butanol, etc.) with optional heating (e.g., 30 to 60° C., preferably 35 to 50° C., preferably 40 to 45° C.) until the benzothiazolium salt of formula I is fully dissolved and a clear solution is formed. Next, the as-prepared thallium doped gadolinium chalcogenide may be dispersed into the clear solution, and the resulting mixture may be optionally heated at 35 to 65° C., preferably 40 to 60° C., preferably 45 to 55° C. for 10 to 60 minutes, preferably 20 to 50 minutes, preferably 30 to 40 minutes. After sufficient reaction has taken place, the solids may then be collected, for example by filtration or centrifugation, for example centrifugation at 5,000 to 15,000 rpm, preferably 8,000 to 12,000 rpm, preferably 10,000 rpm, and subsequently dried under vacuum to afford the fluorescent nanocomposite of the present disclosure. Without being bound by theory, it is believed that the benzothiazolium salt is bound to the thallium doped gadolinium chalcogenide via the sulfur atom of the benzothiazole ring. Evidence for such bonding/coordination can be found in the Fourier-transform infrared spectroscopy (FTIR) spectrum of the fluorescent nanocomposite, whereby both C—S—Gd and C—S—Tl bending vibrations are indicated.

The fluorescent nanocomposite may contain various weight ratios of the benzothiazolium salt of formula I to the thallium doped gadolinium chalcogenide, however, preferred weight ratios of the benzothiazolium salt of formula I to the thallium doped gadolinium chalcogenide range from 1.95:1 to 6.0:1, preferably 2:1 to 5.8:1, preferably 2.2:1 to 5.4:1, preferably 2.4:1 to 5:1, preferably 2.6:1 to 4.5:1, preferably 2.8:1 to 4:1, preferably 3:1 to 3.5:1.

In some embodiments, the benzothiazolium salt of formula I is present in an amount of 65 to 86 wt. %, preferably 66 to 85 wt. %, preferably 68 to 83 wt. %, preferably 70 to 81 wt. %, preferably 72 to 79 wt. %, preferably 74 to 77 wt. %, preferably 75 wt. %, based on a total weight of the fluorescent nanocomposite.

In preferred embodiments, the fluorescent nanocomposite consists of the thallium doped gadolinium chalcogenide and the benzothiazolium salt of formula I. In some embodiments, other quaternary ammonium compounds may be present in the fluorescent nanocomposite, however, preferably, other than the benzothiazolium salt described herein, no other quaternary ammonium compound made from alkylation of an aprotic nitrogenous heteroarene with suitable alkylating agents (e.g., dimethyl sulfate, methyl chloride or bromide, benzyl chloride or bromide) is present in the fluorescent nanocomposite.

In some embodiments, organic functional materials (small molecule organic functional materials) may be included in the fluorescent nanocomposite, however, other than the benzothiazolium salt of formula I, the fluorescent nanocomposite is preferably substantially free of organic functional materials (small molecule organic functional materials) such as those described in US2013/0226268A1 and US 2008/0102311 A1, each incorporated herein by reference in its entirety, with specific mention to host materials, fluorescent emitters (other than the benzothiazolium salt of formula I), phosphorescent emitters, electron transport materials (ETMs), electron injection materials (EIMs), hole injection materials (HIMs), and hole transport materials (HTMs).

In some embodiments, the fluorescent nanocomposite may optionally contain, but is preferably substantially free of polymeric and oligomeric materials, such as epoxy polymers and epoxy oligomers as well as acrylic polymers and oligomers.

In some embodiments, the fluorescent nanocomposite may optionally contain, but is preferably substantially free of clay materials/minerals such as montmorillonite clays (e.g., CLOISITE clays from BYK), including modified clay materials, such as those clays modified with organic materials (e.g., quaternary ammonium compounds).

The fluorescent nanocomposite thus obtained may have a fluorescence emissions peak at 605 to 620 nm, preferably 607 to 618 nm, preferably 609 to 616 nm, preferably 610 to 614 nm, preferably 612 to 613 nm when excited at an excitation wavelength of 450 nm.

It has been found that the resulting fluorescent nanocomposite is extremely sensitive for the detection of antimony ions in various fluids, and is advantageously selective towards antimony ions even when other metal cations are present in abundance. Without being bound by theory, it is believed that selective or preferential binding to antimony ions is responsible for such selective detection. That is, the fluorescent nanocomposite produces a strong fluorescence emission in the absence of antimony (and optionally in the presence of various other non-antimony cations such as potassium, magnesium, iron, arsenic, cobalt, cadmium, mercury, aluminum, and chromium), but upon binding to antimony to form a loaded nanocomposite, the fluorescence emission intensity of the loaded nanocomposite is quenched as a function of the antimony ion concentration. Therefore, the presence/absence of antimony, as well as the concentration of antimony in the fluid sample, can be determined based on the reduction/degree of reduction of the intensity of the fluorescence emissions peak.

A Method of Detecting Antimony Ions

The present disclosure also provides a method of detecting antimony ions in a fluid sample that involves contacting the fluid sample with the fluorescent nanocomposite to form a mixture, and measuring a fluorescence emission profile of the mixture to determine whether antimony is present in the fluid sample and/or to quantify the amount of antimony present in the fluid sample, based on the intensity of the fluorescence emissions peak at 605 to 620 nm as discussed above.

Fluid Sample

The fluid sample that may be analyzed by the methods of the present disclosure is not particularly limited, and may be aqueous, an oil-in-water mixture, or a mixed aqueous and organic solvent mixture. The fluid sample may be obtained from any source that may contain or is suspected of containing antimony ions. In some embodiments, the fluid sample is obtained from a natural water source (lakes, rivers, oceans, aquifers, etc.). In some embodiments, the fluid sample is a wastewater, particularly an industrial wastewater, for example, wastewater produced during automotive manufacturing processes, semiconductor manufacturing processes (e.g., those processes for producing infrared detectors, diodes, etc.), cable sheathing manufacturing operations, battery manufacturing operations, ceramic enamel, paint, and flame-proofing manufacturing processes, and alloying industries, etc.

In some embodiments, the fluid sample is aqueous, and is substantially free of both oil and organic solvent. The aqueous fluid may be fresh water (e.g., water obtained from streams, rivers, lakes, ground water, aquifers, purified water, tap water, well water, wastewater having low salinity such as wastewater deposited into fresh water sources, etc.) or salt water (e.g., seawater, coastal aquifers, or wastewater having high salinity).

In some embodiments, the fluid sample is an oil-in-water mixture, and may contain up to 10%, preferably up to 8%, preferably up to 6%, preferably up to 4%, preferably up to 2%, preferably up to 1% by volume of an oil, based on a total volume of the fluid sample. The oil may include a natural oil, a synthetic oil, or both. Examples of oils from natural sources include, but are not limited to, kerosene, diesel oils, crude oils, gas oils, fuel oils, paraffin oils, mineral oils, low toxicity mineral oils, other petroleum distillates, and any combination thereof. Examples of synthetic oils include, but are not limited to, polyolefins, polydiorganosiloxanes, siloxanes, organosiloxanes, as well as mixtures thereof.

In some embodiments, the fluid sample is a mixed aqueous and organic solvent mixture. The organic solvent that may be optionally present in the fluid sample is not particularly limited, and may include organic solvent(s) employed during various industrial processes that produce a wastewater that may contain or is suspected of containing antimony ions, for example, the manufacturing operations described above. The organic solvent may be miscible or immiscible with water. Exemplary organic solvents that may be present in the fluid sample include, but is not limited to, aromatic solvents (e.g., benzene, ethylbenzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. The fluid sample may contain up to 30%, preferably up to 25%, preferably up to 20%, preferably up to 15%, preferably up to 10%, preferably up to 5%, preferably up to 2%, preferably up to 1% by volume of an organic solvent(s) based on a total volume of the fluid sample. Typically, when an organic solvent is present in the fluid sample, a ratio of water to the organic solvent ranges from 5:1 to 100:1, preferably 6:1 to 75:1, preferably 7:1 to 50:1, preferably 8:1 to 25:1, preferably 9:1 to 15:1.

In addition to optionally containing an oil(s) and/or an organic solvent(s) as described above, the fluid sample may optionally contain suspended solids. In some embodiments, the fluid sample contains greater than 55% v/v of water, preferably greater than 60% v/v of water, preferably greater than 65% v/v of water, preferably greater than 70% v/v of water, preferably greater than 75% v/v of water, preferably greater than 80% v/v of water, preferably greater than 85% v/v of water, preferably greater than 90% v/v of water, preferably greater than 95% v/v of water, preferably greater than 99% v/v of water, based on a total volume of the fluid sample.

The fluid sample may contain antimony ions (e.g., $Sb^{3+}$ and/or $Sb^{5+}$). When present, the antimony ions may be present in the fluid sample at a concentration of 0.00001 to 3,000 mg/L, preferably 0.0001 to 2,500 mg/L, preferably 0.001 to 2,000 mg/L, preferably 0.01 to 1,500 mg/L, preferably 0.05 to 1,000 mg/L, preferably 0.1 to 900 mg/L, preferably 0.5 to 800 mg/L, preferably 1 to 700 mg/L, preferably 5 to 600 mg/L, preferably 10 to 500 mg/L, preferably 20 to 400 mg/L, preferably 40 to 300 mg/L, preferably 60 to 250 mg/L, preferably 80 to 200 mg/L, preferably 100 to 150 mg/L. Examples of antimony species that may be present in the fluid sample, which are in the form of antimony ions or are capable of forming antimony ions in situ include, but are not limited to, antimony(III) acetate, antimony(III) chloride, antimony(V) chloride, antimony(III) fluoride, antimony(V) fluoride, antimony(III) iodide, antimony(III) sulfate, fluoroantimonic acid, nitronium hexafluoroantimonate, nitrosonium hexafluoroantimonate, and potassium antimony(III) tartrate, just to name a few.

The fluid sample may also optionally include one or more (non-antimony) cations, including heavy and transitional metal cations as well as alkali and alkaline earth metal cations, such as cations of sodium, potassium, calcium, magnesium, barium, strontium, rubidium, cesium, iron (ferrous and ferric), arsenic, cobalt, copper, manganese, nickel, zinc, cadmium, mercury, silver, aluminum, gallium, chromium, and lead, including mixtures thereof. Representative examples of anions which may also be present in the fluid sample include, but are not limited to, chloride, carbonate, bicarbonate, sulfate, bromide, iodide, acetate, hydroxide, sulfide, hydrosulfide, chlorate, fluoride, hypochlorite, nitrate, nitrite, perchlorate, peroxide, phosphate, phosphite, sulfite, hydrogen phosphate, hydrogen sulfate, as well as mixtures thereof.

In some embodiments, sodium ions may be present in the fluid sample in amounts of at least 50 ppm, and up to 50,000 ppm, preferably up to 40,000 ppm, preferably up to 30,000 ppm, preferably up to 20,000 ppm, preferably up to 10,000 ppm, preferably up to 5,000 ppm, preferably up to 1,000 ppm, preferably up to 500 ppm, preferably up to 200 ppm.

In some embodiments, potassium ions may be present in the fluid sample in amounts of at least 5 ppm, and up to 20,000 ppm, preferably up to 15,000 ppm, preferably up to 10,000 ppm, preferably up to 5,000 ppm, preferably up to 1,000 ppm, preferably up to 500 ppm, preferably up to 100 ppm.

The fluid sample may also generally contain up to 50,000 ppm of multivalent (non-antimony) cations (e.g., magnesium ions, calcium ions, iron ions, strontium ions, barium ions, lead ions, copper ions, cobalt ions, cadmium ions, mercury ions, manganese ions, nickel ions, zinc ions, arsenic ions, chromium ions, and/or aluminum ions, etc.), for example at least 50 ppm, preferably at least 75 ppm, preferably at least 100 ppm, preferably at least 150 ppm, preferably at least 200 ppm, preferably at least 500 ppm, preferably at least 1,000 ppm, preferably at least 2,000 ppm, preferably at least 5,000 ppm, and up to 50,000 ppm, preferably up to 40,000 ppm, preferably up to 30,000 ppm, preferably up to 20,000 ppm, preferably up to 10,000 ppm, preferably up to 7,000 ppm, preferably up to 6,000 ppm total of multivalent cations. For example, barium and/or strontium ions may be present in the fluid sample in amounts of at least 100 ppm, preferably at least 200 ppm, preferably at least 400 ppm, preferably at least 600 ppm, preferably at least 800 ppm, preferably at least 1,000 ppm, preferably at least 1,200 ppm, preferably at least 1,400 ppm, preferably at least 1,600 ppm, preferably at least 1,800 ppm, preferably at least 2,000 ppm, preferably at least 2,500 ppm, preferably at least 3,000 ppm, preferably at least 4,000 ppm, and up to 10,000 ppm, preferably up to 9,000 ppm, preferably up to 8,000 ppm, preferably up to 7,000 ppm, preferably up to 6,000 ppm, preferably up to 5,000 ppm, preferably up to 4,800 ppm, preferably up to 4,600 ppm. Magnesium ions, for example in amounts up to 2,500 ppm, preferably up to 2,000 ppm, preferably up to 1,500 ppm, preferably up to 1,000 ppm, preferably up to 500 ppm, preferably up to 100 ppm, and/or calcium ions, for example in amounts up to 15,000 ppm, preferably up to 12,000 ppm, preferably up to 10,000 ppm, preferably up to 8,000 ppm, preferably up to 6,000 ppm, preferably up to 4,000 ppm, preferably up to 2,000 ppm, preferably up to 1,000 ppm, preferably up to 500 ppm, may also be present in the fluid sample.

In some embodiments, the fluid sample has a total dissolved solids (TDS) content of up to 200,000 mg/L, for example 100 to 200,000 mg/L, preferably 500 to 180,000 mg/L, preferably 1,000 to 150,000 mg/L, preferably 1,500 to 100,000 mg/L, preferably 2,000 to 80,000 mg/L, preferably 3,000 to 60,000 mg/L, preferably 4,000 to 40,000 mg/L, preferably 5,000 to 20,000 mg/L, preferably 6,000 to 10,000 mg/L.

The fluid sample (and thus the mixture) may contain a surfactant. Alternatively, prior to the contacting, a surfactant may be added to the fluid sample, for example, when the fluid sample to be tested is an oil-in-water mixture (e.g., a wastewater) to better disperse/distribute the fluorescent nanocomposite throughout the fluid sample. The surfactant may be a cationic, anionic, non-ionic, and/or amphoteric surfactant, and may be present in the fluid sample in an amount of up to 5 wt. %, preferably up to 4 wt. %, preferably up to 3 wt. %, preferably up to 2 wt. %, preferably up to 1 wt. %, preferably up to 0.5 wt. %, preferably up to 0.1 wt. %, based on a total weight of the fluid sample.

Cationic surfactants may include, but are not limited to
a protonated amine formed from a reaction between a $C_6$-$C_{26}$ alkyl amine compound and an acid (e.g., acetic acid, formic acid, propionic acid, butyric acid, pentanoic acid, hexanoic acid, oxalic acid, malonic acid, lactic acid, glyceric acid, glycolic acid, malic acid, citric acid, benzoic acid, p-toluenesulfonic acid, trifluoromethanesulfonic acid, hydrochloric acid, nitric acid, phosphoric acid, sulfuric acid, hydrobromic acid, perchloric acid, hydroiodic acid, etc.), such as protonated salts of $C_6$-$C_{26}$ alkyl monoamines, $C_6$-$C_{26}$ alkyl (poly)alkylene polyamines, and alkoxylated fatty amines;

a protonated $C_6$-$C_{26}$ alkyl amidoamine formed from a reaction between a $C_6$-$C_{26}$ alkyl amidoamine compound and an acid (for example the acids listed above), such as protonated forms of the amide reaction product between any fatty acid previously listed (or ester derivative thereof) with a polyamine (e.g., putrescine, cadaverine, ethylene diamine, $N^1,N^1$-dimethylethane-1,2-diamine, $N^1,N^1$-dimethylpropane-1,3-diamine, $N^1,N^1$-diethylethane-1,2-diamine, $N^1,N^1$-diethylpropane-1,3-diamine, spermidine, 1,1,1-tris(aminomethyl) ethane, tris(2-aminoethyl)amine, spermine, TEPA, DETA, TETA, AEEA, PEHA, HEHA, dipropylene triamine, tripropylene tetramine, tetrapropylene pentamine, pentapropylene hexamine, hexapropylene heptamine, dibutylene triamine, tributylene tetramine, tetrabutylene pentamine, pentabutylene hexamine, hexabutylene heptamine), with specific mention being made to protonated forms of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, and arachidamidoethyldimethylamine; and a quaternary ammonium compound made from alkylation with suitable alkylating agents (e.g., dimethyl sulfate, methyl chloride or bromide, benzyl chloride or bromide, $C_6$-$C_{26}$ alkyl chloride or bromide, etc.) of a tertiary $C_6$-$C_{26}$ alkyl amine, an alkoxylated (tertiary) amine, or an aprotic nitrogenous heteroarene (optionally substituted) having at least one aromatic nitrogen atom with a reactive lone pair of electrons, with specific mention being made to a tri-fatty alkyl lower alkyl ammonium compound (e.g., trioctyl methyl ammonium chloride), a $C_{10}$-$C_{18}$ alkyl trimethyl ammonium chloride or methosulfate, a di-$C_{10}$-$C_{18}$ alkyl dimethyl ammonium chloride or methesulfate, a $C_{10}$-$C_{18}$ alkyl benzyl dimethyl ammonium chloride, a methyl quaternized $C_6$-$C_{22}$ alkyl propylene diamine, a methyl quaternized $C_6$-$C_{22}$ alkyl propylene triamine, a methyl quaternized $C_6$-$C_{22}$ alkyl propylene tetraamine, a N—$C_{10}$-$C_{18}$ alkyl pyridinium or a quinolinium bromide or chloride such as N-octyl pyridinium bromide, N-nonyl pyridinium bromide, N-decyl pyridinium bromide, N-dodecyl pyridinium bromide, N-tetradecyl pyridinium bromide, N-dodecyl pyridinium chloride, N-cyclohexyl pyridinium bromide, naphthyl methyl quinolinium chloride, naphthyl methyl pyridinium chloride, and cetylpyridinium chloride (for example those disclosed in CN101544903B—incorporated herein by reference in its entirety);

as well as mixtures thereof.

Anionic surfactants may include, but are not limited to:
sulfates, such as alkyl sulfates, alkyl-ester-sulfates, alkyl ether sulfates, alkyl-alkoxy-ester-sulfate, sulfated alkanolamides, glyceride sulfates, in particular, sulfates of fatty alcohols or polyoxyalkylene ethers of fatty alcohols such as sodium dodecyl sulfate, sodium laureth sulfate, ammonium lauryl sulfate, potassium lauryl sulfate, sodium myreth sulfate;

sulfonates such as alkyl sulfonates, fatty alkyl-benzene sulfonates, lower alkyl-benzene sulfonates, alpha olefin sulfonates, lignosulfonates, sulfo-carboxylic compounds, for example, dodecyl benzene sulfonate, dioctyl sodium sulfosuccinate, perfluorooctanesulfonate (PFOS), perfluorobutanesulfonate;

phosphates such as alkyl aryl ether phosphates, alkyl ether phosphates, phosphates of fatty alcohols or polyoxyalkylene ethers of fatty alcohols such as cetyl phosphate salts, dicetyl phosphate salts, ceteth-10-phosphate salts;

carboxylate salts of fatty acids, acylamino acids, lactylates, and/or fatty alcohols/polyoxyalkylene ethers of fatty alcohols such as sodium stearate, vegetable oil-based anionic surfactants (e.g., palm oil anionic surfactant), sodium behenoyl lactylate, sodium isostearoyl lactylate, sodium caproyl lactylate, sodium laureth-5 carboxylate, sodium laureth-6 carboxylate, sodium laureth-11 carboxylate;

and mixtures thereof.

Non-ionic surfactants may include, but are not limited to:
amides or alkanolamides of fatty acids, that is, amide reaction products between a fatty acid and an amine or alkanolamine compound, such as coconut fatty acid monoethanolamide (e.g., N-methyl coco fatty ethanol amide), coconut fatty acid diethanolamide, oleic acid diethanolamide, palm based oleylamine, and vegetable oil fatty acid diethanolamide;

alkoxylated alkanolamides of fatty acids, preferably ethoxylated and/or propoxylated variants of the alkanolamides of fatty acids using for example anywhere from 2 to 30 EO and/or PO molar equivalents, preferably 3 to 15 EO and/or PO molar equivalents, preferably 4 to 10 EO and/or PO molar equivalents, preferably 5 to 8 EO and/or PO molar equivalents per moles of the alkanolamide of the fatty acid (e.g., coconut fatty acid monoethanolamide with 4 moles of ethylene oxide);

amine oxides, such as N-cocoamidopropyl dimethyl amine oxide and dimethyl $C_6$-$C_{22}$ alkyl amine oxide (e.g., dimethyl coco amine oxide);

fatty esters, such as ethoxylated and/or propoxylated fatty acids (e.g., castor oil with 2 to 40 moles of ethylene oxide), alkoxylated glycerides (e.g., PEG-24 glyceryl monostearate), glycol esters and derivatives, monoglycerides, polyglyceryl esters, esters of polyalcohols, and sorbitan/sorbitol esters;

ethers, such as (i) alkoxylated $C_1$-$C_{22}$ alkanols, which may include alkoxylated $C_1$-$C_5$ alkanols, preferably ethoxylated or propoxylated $C_1$-$C_5$ alkanols (e.g., dipropylene glycol n-butyl ether, tripropylene glycol n-butyl ether, dipropylene glycol methyl ether, tripropylene glycol methyl ether, diethylene glycol n-butyl ether, triethylene glycol n-butyl ether, diethylene glycol methyl ether, triethylene glycol methyl ether) and alkoxylated $C_6$-$C_{26}$ alkanols (including alkoxylated fatty alcohols), preferably alkoxylated $C_7$-$C_{22}$ alkanols, more preferably alkoxylated $C_8$-$C_{14}$ alkanols, preferably ethoxylated or propoxylated (e.g., cetyl stearyl alcohol with 2 to 40 moles of ethylene oxide, lauric alcohol with 2 to 40 moles of ethylene oxide, oleic alcohol with 2 to 40 moles of ethylene oxide, ethoxylated lanoline derivatives, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether); (ii) alkoxylated polysiloxanes; (iii) ethylene oxide/propylene oxide copolymers (e.g., PPG-1-PEG-9-lauryl glycol ether, PPG-12-buteth-16, PPG-3-buteth-5, PPG-5-buteth-7, PPG-7-buteth-10, PPG-9-buteth-12, PPG-12-buteth-16, PPG-15-buteth-20, PPG-20-buteth-30, PPG-28-buteth-35, and PPG-33-buteth-45); and (iv) alkoxylated alkylphenols;

alkyl polyglycosides (APGs) such as those made from reaction between fatty alcohols and glucose;

and mixtures thereof.

Amphoteric surfactants may include, but are not limited to:

$C_6$-$C_{22}$ alkyl dialkyl betaines, such as fatty dimethyl betaines (R—N(CH$_3$)$_2$($^+$)—CH$_2$COO$^-$), obtained from a $C_6$-$C_{22}$ alkyl dimethyl amine which is reacted with a monohaloacetate salt (e.g., sodium monochloroacetate), such as $C_2$-$C_{14}$ dimethyl betaine (carboxylate methyl $C_{12}$-$C_{14}$ alkyl dimethylammonium);

$C_6$-$C_{22}$ alkyl amido betaines (R—CO—NH—CH$_2$CH$_2$CH$_2$—N(CH$_3$)$_2$($^+$)—CH$_2$COO$^-$ or R—CO—NH—CH$_2$CH$_2$—N(CH$_3$)$_2$($^+$)—CH$_2$COO$^-$), obtained by the reaction of a monohaloacetate salt (e.g., sodium monochloroacetate) with the reaction product of either dimethyl amino propylamine or dimethyl amino ethylamine with a suitable carboxylic acid or ester derivatives thereof, such as $C_{10}$-$C_{18}$ amidopropyl dimethylamino betaine;

$C_6$-$C_{22}$ alkyl sultaines or $C_6$-$C_{22}$ alkyl amido sultaines, which are similar to those $C_6$-$C_{22}$ alkyl dialkyl betaines or $C_6$-$C_{22}$ alkyl amido betaines described above except in which the carboxylic group has been substituted by a sulfonic group (R—N(CH$_3$)$_2$($^+$)—CH$_2$CH$_2$CH$_2$SO$_3^-$ or R—CO—NH—CH$_2$CH$_2$CH$_2$—N(CH$_3$)$_2$($^+$)—CH$_2$CH$_2$CH$_2$SO$_3^-$ or R—CO—NH—CH$_2$CH$_2$—N(CH$_3$)$_2$($^+$)—CH$_2$CH$_2$CH$_2$SO$_3^-$) or a hydroxysulfonic group (R—N(CH$_3$)$_2$($^+$)—CH$_2$CH(OH)—CH$_2$SO$_3^-$ or R—CO—NH—CH$_2$CH$_2$CH$_2$—N(CH$_3$)$_2$($^+$)—CH$_2$CH(OH)—CH$_2$SO$_3^-$ or R—CO—NH—CH$_2$CH$_2$—N(CH$_3$)$_2$($^+$)—CH$_2$CH(OH)—CH$_2$SO$_3^-$), such as $C_{10}$-$C_{18}$ dimethyl hydroxysultaine and $C_{10}$-$C_{18}$ amido propyl dimethylamino hydroxysultaine;

and mixtures thereof.

Contacting

The fluid sample may be contacted with the fluorescent nanocomposite to form the mixture using any method known to those of ordinary skill in the art. For example, the fluid sample may be added to fluorescent nanocomposite or the fluorescent nanocomposite may be added to the fluid sample. The fluorescent nanocomposite may be in the form of a solid or may be formed into a solution prior to the contacting. After combining the fluid sample with the fluorescent nanocomposite, the methods herein may involve manual stirring, mechanical stirring, shaking, blending, mixing, swirling, circulation techniques, sonication (e.g., ultrasonication), or any other agitation technique to form a mixture, preferably a homogenous mixture.

Any amount of the fluorescent nanocomposite may be contacted with the fluid sample that provides a reproducible and accurate fluorescence emissions readout. Typically, the fluorescent nanocomposite is employed in an amount of 0.1 to 50 mg, preferably 0.5 to 25 mg, preferably 1 to 20 mg, preferably 2 to 15 mg, preferably 3 to 10 mg, preferably 4 to 9 mg, preferably 5 to 8 mg, preferably 6 to 7 mg per 1 mL of the fluid sample. Preferably, the fluorescent nanocomposite is the only antimony-specific chemosensor present in the mixture. Preferably, the fluorescent nanocomposite is the only chemosensor present in the mixture.

In some embodiments, the fluid sample is added to the fluorescent nanocomposite as a single portion, or vice versa. Alternatively, the fluid sample may be added dropwise or portion wise (e.g., titrated) into the fluorescent nanocomposite with concomitant agitation, whereby the fluorescence emission profile of the mixture is optionally measured subsequent to each drop/portion of the fluid sample added. Such a procedure may be employed, for example, when it is desired to determine a concentration of antimony ions in the fluid sample by generating a titration curve.

The methods herein enable ultra-fast detection of antimony ions in a fluid sample, and extremely short contacting times may be used. In some embodiments, the fluorescent nanocomposite is contacted with the fluid sample for 1 second to 15 minutes, preferably 5 seconds to 10 minutes, preferably 10 seconds to 8 minutes, preferably 30 seconds to 5 minutes, preferably 1 minute to 2 minutes, prior to the measuring. Of course, longer or shorter contacting times may also be employed, as appropriate.

Mixture

One particular advantage of the fluorescent nanocomposite of the present disclosure is its photostability in a broad pH range. It has been found that the disclosed fluorescent nanocomposite maintains its fluorescence emissions intensity, and thus can be employed for the detection of antimony, in pH conditions ranging from 2 to 11, preferably 3 to 10, preferably 4 to 9, preferably 5 to 8, preferably 6 to 7. Therefore, the use of buffers is not a requirement in the methods herein. However, in some embodiments, a buffer may be optionally added to the fluid sample to ensure the resulting mixture has a suitable pH. The buffer may be optionally added to the fluid sample to provide a concentration in the mixture of 1 to 50 mM, preferably 2 to 45 mM, preferably 3 to 40 mM, preferably 4 to 35 mM, preferably 5 to 30 mM, preferably 6 to 25 mM, preferably 7 to 20 mM, preferably 8 to 15 mM, preferably 9 to 12 mM, preferably 10 to 11 mM, based on a total volume of the mixture.

The buffer may be a phosphate buffer, a borate buffer, a citrate buffer, an acetate buffer, a sulfonic acid buffer (in particular a zwitterionic sulfonic acid buffer), an amino alcohol-based buffer, an arsenate buffer, as well as mixtures thereof. Specific examples of buffers that may be utilized herein include, but are not limited to, monosodium phosphate, monopotassium phosphate, disodium phosphate, citric acid, acetic acid, borate, N-cyclohexyl-2-aminoethanesulfonic acid (CHES), tris(hydroxymethyl)methylamino] propanesulfonic acid (TAPS), 2-(bis(2-hydroxyethyl)amino) acetic acid (bicine), tris(hydroxymethyl)aminomethane) (tris), 3-[N-tris(hydroxymethyl)methylamino]-2-hydroxypropanesulfonic acid (tricine), 3-[N-tris(hydroxymethyl) methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), piperazine-N,N'-bis(2-ethanesulfonic acid) (MOPS), piperazine-N,N'-bis(2-ethanesulfonic acid) (PIPES), dimethylarsenic acid (cacodylate), 2-(N-morpholino)ethanesulfonic acid (MES), bis-tris methane, N-(2-acetamido)iminodiacetic acid (ADA), N-(2-acetamido)-2-aminoethanesulfonic acid (ACES), 3-morpholino-2-hydroxypropanesulfonic acid (MOPSO), cholamine chloride hydrochloride, triethanolamine, 3-[4-(2-hydroxyethyl)piperazin-1-yl]propane-1-sulfonic acid (HEPPS), N-(2-hydroxyethyl)piperazine-N'-(4-butanesulfonic acid (HEPBS), aminomethyl propanol (AMP), including mixtures thereof. In preferred embodiments, the buffer is 4-(2-hydroxyethyl)-1-piperazineethanesulfonic acid (HEPES).

Another particular advantage of the fluorescent nanocomposite of the present disclosure is its photostability under a broad range of temperatures. It has been found that the disclosed fluorescent nanocomposite maintains its fluorescence emissions intensity, and thus can be employed for the detection of antimony, in mixtures having a temperature ranging from 5 to 85° C., preferably 10 to 80° C., preferably 15 to 75° C., preferably 20 to 70° C., preferably 25 to 65° C., preferably 30 to 60° C., preferably 35 to 55° C., preferably 40 to 50° C.

Another particular advantage of the fluorescent nanocomposite of the present disclosure is its prolonged stability, even in solution, under standard storage conditions (e.g., 5° C.). It has been found that the disclosed fluorescent nanocomposite maintains its fluorescence emissions intensity, and thus can be employed for the detection of antimony, even after storage times of up to 24 months, preferably up to 20 months, preferably up to 18 months, preferably up to 16 months, preferably up to 14 months, preferably up to 12 months, and in most cases the fluorescent nanocomposite can be stored in solution for even longer storage times than those listed above.

Measurements

The detection of antimony ions in the fluid sample can be accomplished using fluorescence emissions techniques.

In some embodiments, after forming the mixture, a fluorescence emission profile of the mixture is measured at an excitation wavelength ($\lambda_{ex}$) of 450 nm to determine a presence or absence of antimony ions in the fluid sample. In some embodiments, the fluorescent nanocomposite has a fluorescence emission peak at 605 to 620 nm, preferably 607 to 618 nm, preferably 609 to 616 nm, preferably 610 to 614 nm, preferably 612 to 613 nm. The fluorescence emissions peak has a maximum intensity in the absence of antimony, and, upon being exposed to antimony ions, a reduction of the intensity of the fluorescence emission peak ensues.

In some embodiments, the method may first involve measuring or otherwise obtaining a fluorescence emission profile of the fluorescent nanocomposite in a blank sample (which contains no antimony ions) of equal volume to the fluid sample volume to be tested. Then, after contacting the fluorescent nanocomposite with the fluid sample to form the mixture, the fluorescence emission profile of the mixture can be measured and directly compared to that obtained from the blank sample. Such a comparative analysis may advantageously provide accurate and reliable antimony ion detection.

Therefore, the presence of antimony ions in the fluid sample may be indicated by measuring or monitoring for a reduced intensity of the fluorescence emission peak associated with the fluorescent nanocomposite, for example, by comparing the measured intensity to that of a blank sample in which no antimony ions are present. If the intensity of the fluorescence emission peak (e.g., at 605 to 620 nm) of the mixture is the same or substantially the same (e.g., intensity difference of 2% or less, 1% or less, 0.5% or less, 0.1% or less) as that of the blank sample, then it can be determined that no antimony ions are present in the mixture (and thus the fluid sample). On the other hand, if the intensity of the fluorescence emission peak (e.g., at 605 to 620 nm) of the mixture is reduced (e.g., intensity is reduced by more than 2%, more than 3%, more than 4%, more than 5%, more than 10%, more than 15%, more than 20%, more than 30%, etc.) compared to that of the blank sample, then it can be determined that antimony ions are present in the mixture (and thus the fluid sample).

In some embodiments, the method further involves determining/quantifying a concentration of the antimony ions in the fluid sample. This may be accomplished by measuring a relative intensity of the mixture ($I_0/I$), defined as a ratio of a maximum fluorescence intensity of the fluorescent nanocomposite in a blank sample devoid of antimony ions ($I_0$) to a maximum fluorescence intensity of the mixture (I), and comparing to a calibration curve that relates antimony ion concentration to relative intensity ($I_0/I$). For example, an initial fluorescence intensity readout ($I_0$) of the emissions peak at 605 to 620 nm of the fluorescent nanocomposite in a blank sample may be obtained, then the fluid sample may be titrated into the fluorescent nanocomposite to form the mixture, and the fluorescence intensity of the emissions peak at 605 to 620 nm may be measured after each addition (I). The relative intensity of the mixture ($I_0/I$) after each addition may be plotted as a function of concentration, and the concentration of antimony ions in the fluid sample may then be calculated by comparing the plot to a calibration curve formed using known concentrations of antimony ions, as is known to those of ordinary skill in the art.

The methods of the present disclosure are preferably selective for the detection of antimony ions, that is, only the presence of antimony ions in the mixture produces a reduced intensity readout at the fluorescence emission peak around 605 to 620 nm. For example, cations other than antimony which may be present in the fluid sample, including but not limited to, cations of sodium, potassium, calcium, magnesium, barium, strontium, rubidium, cesium, iron (ferrous and ferric), arsenic, cobalt, copper, manganese, nickel, zinc, cadmium, mercury, silver, aluminum, gallium, chromium, lead, and mixtures thereof, do not cause a substantial fluorescence intensity reduction when combined with the fluorescent nanocomposite. For example, such non-antimony cations reduce the measured intensity by 2% or less, 1% or less, 0.5% or less, 0.1% or less, even when present at 100-fold higher concentrations (or more) than antimony.

In some embodiments, non-antimony cations (e.g., one or more cations of sodium, potassium, calcium, magnesium, barium, strontium, rubidium, cesium, iron (ferrous and ferric), arsenic, cobalt, copper, manganese, nickel, zinc, cadmium, mercury, silver, aluminum, gallium, chromium, and lead) produce a relative intensity ($I_0/I$) of less than 1.5, preferably less than 1.4, preferably less than 1.3, preferably less than 1.2, preferably less than 1.1, when present in the mixture in a concentration of 100 mg/L. Whereas antimony ions, when present in the mixture at a concentration of 100 mg/L, preferably produce a relative intensity ($I_0/I$) of 9 to 10, preferably 9.2 to 9.8, preferably 9.4 to 9.6, preferably 9.5. The change in relative intensity ($I_0/1$) between antimony cations and non-antimony cations enables extremely accurate and facile antimony ion detection and/or antimony ion concentration determination, even in the presence of various other cations.

Indeed, the methods herein may have a antimony ion detection lower limit of 0.00001 to 0.0001 mg/L, preferably 0.00002 to 0.00008 mg/L, preferably 0.00004 to 0.00006 mg/L, preferably 0.00005 mg/L.

A Method of Removing Antimony Ions

The present disclosure also provides a method of removing antimony ions from a fluid sample. In such removal methods, after forming the mixture as described above, whereby antimony ions adsorb onto the fluorescent nanocomposite to form a loaded nanocomposite, the loaded nanocomposite may be separated from the mixture by centrifugation and/or filtration.

For example, the fluorescent nanocomposite may be contacted with a fluid sample containing antimony ions to form a mixture, and the mixture may be agitated (e.g., sonicated) for 1 to 30 minutes, preferably 2 to 25 minutes, preferably 4 to 20 minutes, preferably 6 to 15 minutes, preferably 8 to 10 minutes to form the loaded nanocomposite.

The loaded nanocomposite may then be separated from the mixture via one or more solid-liquid separation techniques/devices, including, but not limited to a dissolved air flotation (DAF) device; an induced air flotation (IAF) device; a settling tank; a flocculation device using induced velocity gradients generated from baffled chambers, granular media beads, spiral flow chambers, reciprocating blades, and/or rotating blades; a centrifuge such as a stacked disc centrifuge, a horizontal solid bowl centrifuge, a decanter, a tricanter; a recessed chamber filter press; a rotary drum vacuum filter or other vacuum filter; a belt press; a pressure filter; a membrane filtration device; parallel plate separators; a hydrocyclone; walnut shell filters; and media filters. In preferred embodiments, the loaded nanocomposite is separated from the mixture via centrifugation, preferably by centrifuging the mixture at 10,000 to 20,000 rpm, preferably 12,000 to 18,000 rpm, preferably 14,000 to 16,000 rpm, and the loaded nanocomposite can be optionally recovered by drying for example at 20 to 70° C., preferably 25 to 60° C., preferably 30 to 50° C.

In doing so, a concentration of antimony ions in the fluid sample after the contacting and separating is lower than an initial concentration of antimony ions in the fluid sample. In some embodiments, the method herein removes at least 80%, preferably at least 85%, preferably at least 90%, preferably at least 95%, preferably at least 99%, preferably at least 99.5% of the antimony ions by weight, based on an initial weight of the antimony ions in the fluid sample, as determined for example by inductively coupled plasma atomic emission spectroscopy (ICP-AES).

The examples below are intended to further illustrate protocols for preparing the fluorescent nanocomposite and for detecting/removing antimony ions in/from fluid samples using the fluorescent nanocomposite, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Example 1

Preparation of $Tl_{0.05}Gd_{0.95}S$ Quantum Dots

Figure 2:
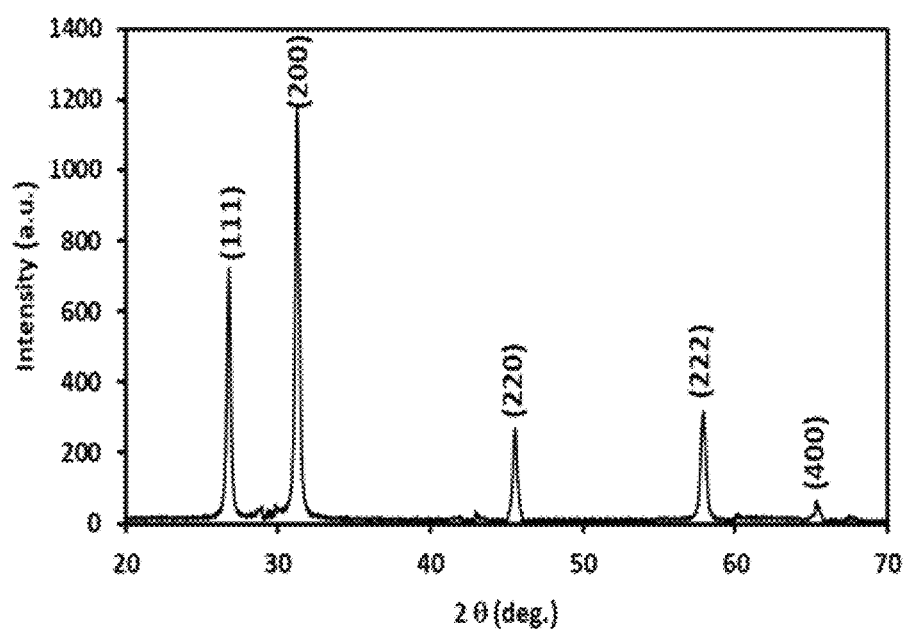
FIG. 2 illustrates the XRD patterns of the prepared $Tl_{0.05}Gd_{0.95}S$ nanoparticles.

About 25 mg of tris(cyclopentadienyl)gadolinium and 0.42 mg of thallium pentafluoropropionate was inserted in a three-neck flask and dissolved in 80 ml of 1,2-ethanediol. The mixture was heated to 90° C. for 45 min under nitrogen gas umbrella. Then, 3 mL of phenyl(trifluoromethyl)sulfide (1.3 mM) was injected quickly. After injection, the temperature of the whole mixture was raised to 140° C. and kept refluxing for 60 min. Then after, the reaction was stopped via quenching the flask in ice bath at 4° C. for 10 min. The suspension was collected via centrifugation at 14000 rpm for 10 min. The supernatant was collected and washed by acetone and 2-propanol to remove the excess of 1,2-ethanediol and centrifuged again at 7000 rpm for 6 min. The product was dried at 60° C. for 8h. FIG. 1 shows the TEM image of the final product. The nanoparticle product has a spherical like shape with a mean size of 5±2 nm. FIG. 2 shows the XRD of the prepared $Tl_{0.05}Gd_{0.95}S$ nanoparticles. All patterns matched well the cubic phase of GdS (JCPDS-Card no. 26-1423). There are no other peaks corresponding to gadolinium or thallium or sulfur compounds in the XRD patterns, implying the dissolving of the thallium atoms into the gadolinium sulfide crystal structure.

Example 2

Figure 3:
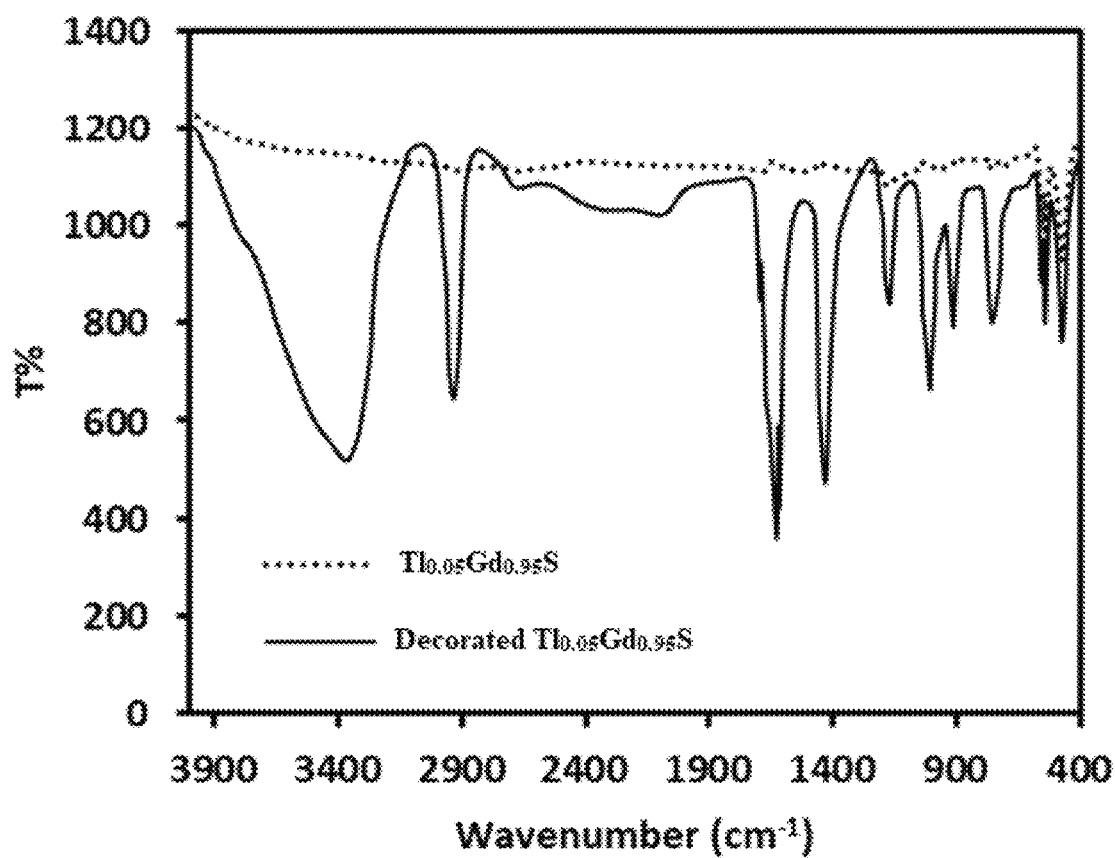
FIG. 3 illustrates the FTIR spectra of the $Tl_{0.05}Gd_{0.95}S$ nanoparticles before and after surface decoration with 2-(4-(dimethylamino)styryl)-3-ethyl-benzothiazolium.

The Surface Decoration of $Tl_{0.05}Gd_{0.95}S$ by 2-(4-(Dimethylamino)Styryl)-3-Ethyl-Benzothiazolium About 90 mg of the 2-(4-(dimethylamino)styryl)-3-ethyl-benzothiazolium bromide was dissolved in 5 ml of ethanol at temperature of 35° C. until clear and homogenous solution was formed. The as-prepared $Tl_{0.05}Gd_{0.95}S$ (30 mg) was dispersed into the 2-(4-(dimethylamino)styryl)-3-ethyl-benzothiazolium bromide solution and refluxed at 45° C. for 40 min. The product was collected through centrifuging at 10000 rpm for 8 min and left to dry under vacuum. FIG. 3 depicts the FTIR spectra of the $Tl_{0.05}Gd_{0.95}S$ nanoparticles before and after the surface decoration with 2-(4-(dimethylamino)styryl)-3-ethyl-benzothiazolium. The $Tl_{0.05}Gd_{0.95}S$ before decoration showed two bands at 575 $cm^{-1}$ and 491 $cm^{-1}$ which assigned to Gd—S and Gd—S—Tl bending vibrations. The IR spectra for the after decoration with 2-(4-(dimethylamino)styryl)-3-ethyl-benzothiazolium showed absorption bands at 3513 $cm^{-1}$ 2891 $cm^{-1}$, 2846 $cm^{-1}$, 2611 $cm^{-1}$, 1642 $cm^{-1}$, 1391 $cm^{-1}$, 1168 $cm^{-1}$, 1019 $cm^{-1}$ and 765 $cm^{-1}$ are assigned to the stretching vibrations of O—H and N—H, symmetric C—H, asymmetric C—H, S—C, C—C, H—C—H groups and the bending vibrations of C—O, C—S—Tl, C—S—Gd groups, respectively. This implying that the 2-(4-(dimethylamino)styryl)-3-ethyl-benzothiazolium attached to the surface of the $Tl_{0.05}Gd_{0.95}S$ nanoparticles.

Example 3

Figure 4:
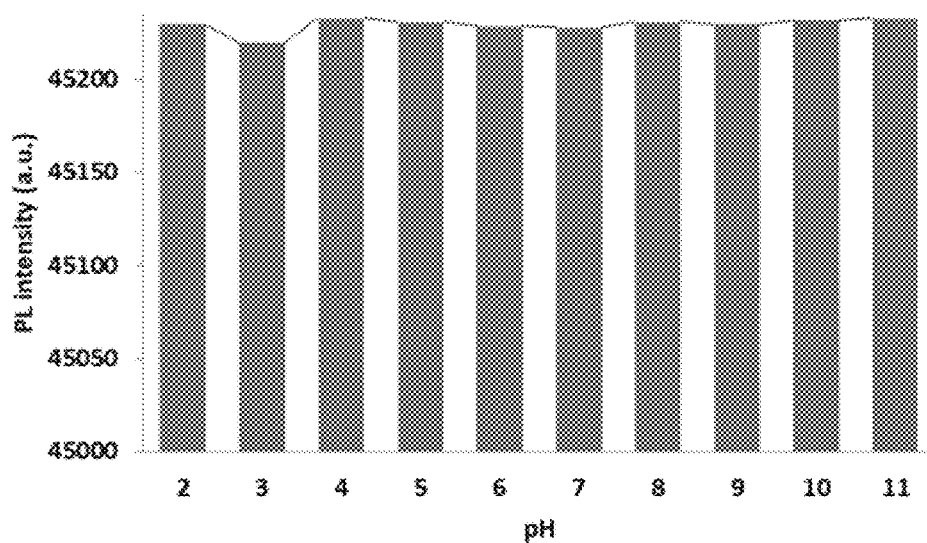
FIG. 4 illustrates the luminescence intensity of the decorated $Tl_{0.05}Gd_{0.95}S$ nanoparticles with 2-(4-(dimethylamino)styryl)-3-ethyl-benzothiazolium at different pH values.

The Photostability of the $Tl_{0.05}Gd_{0.95}S$ Decorated 2-(4-(Dimethylamino)Styryl)-3-Ethyl-Benzothiazolium in Alkaline and Acidic Media Water soluble $Tl_{0.05}Gd_{0.95}S$ nanoparticles decorated with 2-(4-(dimethylamino)styryl)-3-ethyl-benzothiazolium were made by dispersing 20 mg of the decorated $Tl_{0.05}Gd_{0.95}S$ nanoparticles in 40 ml of deionized water followed by sonication for 20 min at a temperature of 22° C. The pH value of this solution was changed from 2 to 6 by adding HCl (2M) from 3 ml to 0.35 ml. The pH value of this solution was changed from 8 to 11 by adding NaOH (2M) from 0.42 to 1.33 ml to the water soluble decorated $Tl_{0.05}Gd_{0.95}S$ nanoparticles. The luminescence spectra were monitored using Perkin Elmer LS-55 Spectrometer. The slit width was adjusted at 1.4 nm at wavelength of 450 nm. FIG. 4 shows the effect of pH on the fluorescence intensity of the $Tl_{0.05}Gd_{0.95}S$ nanoparticles decorated with 2-(4-(dimethylamino)styryl)-3-ethyl-benzothiazolium. The fluorescence intensity was not changed and kept constant at 41200±80 along the pH range from 2 to 11, implying the high photostability of the $Tl_{0.05}Gd_{0.95}S$ nanoparticles decorated with 2-(4-(dimethylamino)styryl)-3-ethyl-benzothiazolium in the acidic and alkaline media.

Example 4

Figure 5:
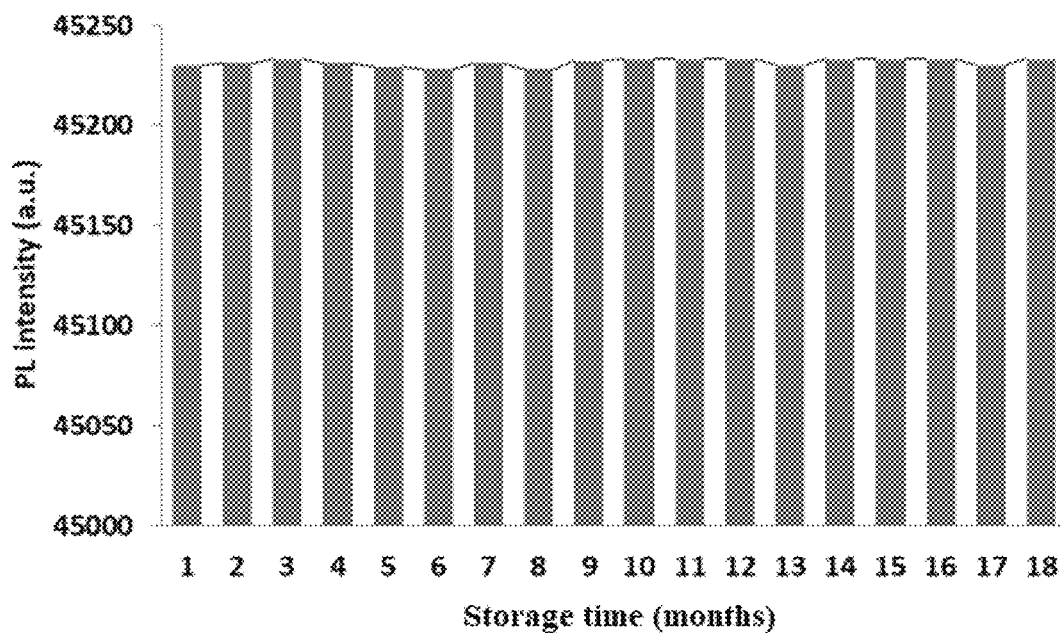
FIG. 5 illustrates the luminescence intensity of the decorated $Tl_{0.05}Gd_{0.95}S$ nanoparticles with 2-(4-(dimethylamino)styryl)-3-ethyl-benzothiazolium at different storage times.

The Photostability of the $Tl_{0.05}Gd_{0.95}S$ Decorated 2-(4-(Dimethylamino)Styryl)-3-Ethyl-Benzothiazolium Against Storage Time Water soluble $Tl_{0.05}Gd_{0.95}S$ nanoparticles decorated with 2-(4-(dimethylamino)styryl)-3-ethyl-benzothiazolium were made by dispersing 20 mg of the decorated $Tl_{0.05}Gd_{0.95}S$ nanoparticles in 40 ml of deionized water followed by sonication for 20 min at a temperature of 22° C. The prepared solution was stored in a refrigerator at 5° C. for 18 months. The fluorescence of the $Tl_{0.05}Gd_{0.95}S$ nanoparticles decorated with 2-(4-(dimethylamino)styryl)-3-ethyl-benzothiazolium solution was monitored along such a period of time for 18 months at the same conditions presented in Example 3. FIG. 5 shows the impact of the storage time on the fluorescence intensity of the $Tl_{0.05}Gd_{0.95}S$ nanoparticles decorated with 2-(4-(dimethylamino)styryl)-3-ethyl-benzothiazolium. The fluorescence intensity showed fixed value at 41200±30 from 1 to 18 months, implying the high photostability of the $Tl_{0.05}Gd_{0.95}S$ nanoparticles decorated with 2-(4-(dimethylamino)styryl)-3-ethyl-benzothiazolium against storage time.

Example 5

Figure 6:
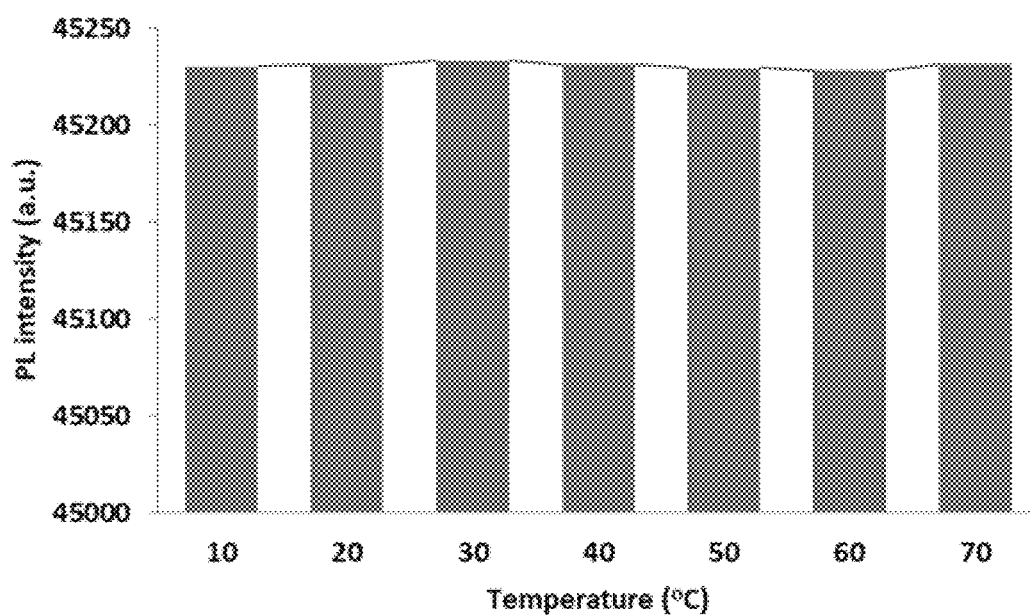
FIG. 6 illustrates the luminescence intensity of the decorated $Tl_{0.05}Gd_{0.95}S$ nanoparticles with 2-(4-(dimethylamino)styryl)-3-ethyl-benzothiazolium at different temperatures.

The Photostability of the $Tl_{0.05}Gd_{0.95}S$ Decorated 2-(4-(Dimethylamino)Styryl)-3-Ethyl-Benzothiazolium Against Temperature Water soluble $Tl_{0.05}Gd_{0.95}S$ nanoparticles decorated with 2-(4-(dimethylamino)styryl)-3-ethyl-benzothiazolium were made by dispersing 20 mg of the decorated $Tl_{0.05}Gd_{0.95}S$ nanoparticles in 40 ml of deionized water followed by sonication for 20 min at a temperature of 22° C. The temperature of the $Tl_{0.05}Gd_{0.95}S$ nanoparticles decorated with 2-(4-(dimethylamino)styryl)-3-ethyl-benzothiazolium solution was raised to 70° C. The fluorescence intensity of the solution was monitored along the temperature range from 10° C. to 70° C. at the same conditions presented in Example 3. FIG. 6 shows the effect of the temperature on the fluorescence intensity of the $Tl_{0.05}Gd_{0.95}S$ nanoparticles decorated with 2-(4-(dimethylamino)styryl)-3-ethyl-benzothiazolium. The fluorescence intensity showed a fixed value of 41190±50 along the temperature range from 10° C. to 70° C., implying the high photostability of the $Tl_{0.05}Gd_{0.95}S$ nanoparticles decorated with 2-(4-(dimethylamino)styryl)-3-ethyl-benzothiazolium against temperature.

Example 6

Preparation of Antimony Solution in Water 1000 mg of nitronium hexafluoroantimonate was dissolved in 1 L of deionized water to obtain an antimony solution of 1000 mg/L. This standard antimony solution was further diluted to get solutions of different concentrations of antimony (0.001 mg/L, 0.01 mg/L, 0.1 mg/L, 1 mg/L, 10 mg/L, 100 mg/L and 1000 mg/L).

Example 7

Detection of Antimony in Water

Figure 7A:
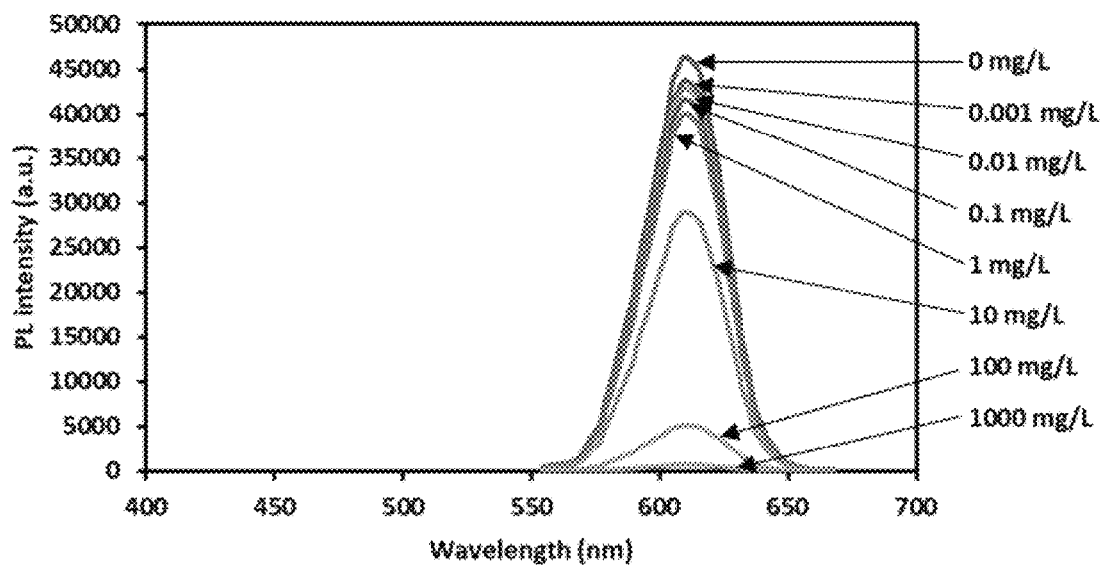
FIGS. 7A and 7B illustrate the luminescence spectra of the decorated $Tl_{0.05}Gd_{0.95}S$ nanoparticles with 2-(4-(dimethylamino)styryl)-3-ethyl-benzothiazolium at different antimony concentrations in water (7A) and the calibration curve of the relative luminescence intensity $(I_0/I)$ against antimony concentrations in water (7B)
Figure 7B:
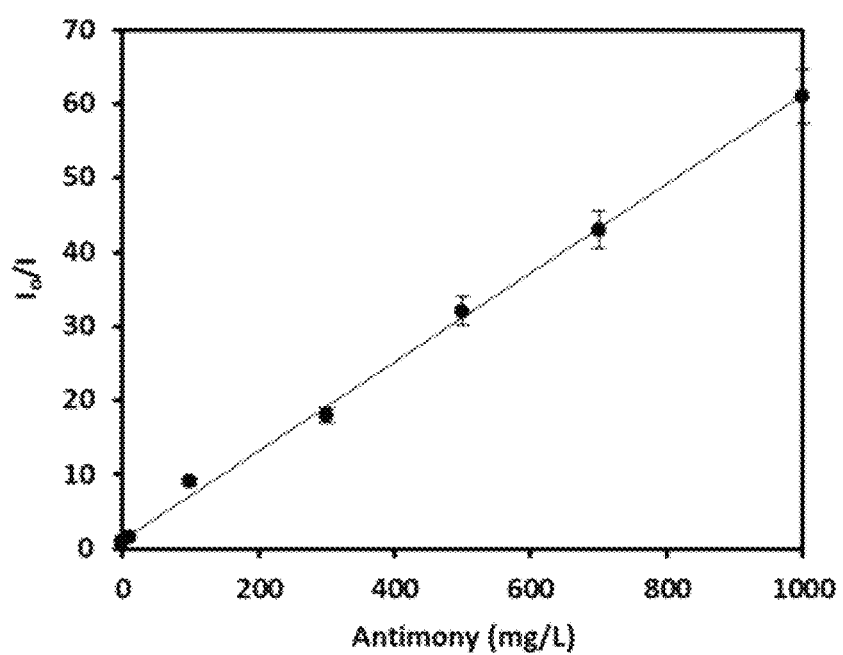

To each 10 ml of the contaminated water with antimony with concentrations of 0.001 mg/L, 0.01 mg/L, 0.1 mg/L, 1 mg/L, 10 mg/L, 100 mg/L and 1000 mg/L, 50 mg of the $Tl_{0.05}Gd_{0.95}S$ nanoparticles decorated with 2-(4-(dimethylamino)styryl)-3-ethyl-benzothiazolium were added and sonicated for 15 min at T=22° C. The fluorescence intensity was detected by Perkin Elmer LS-55 Spectrometer. The slit width was 1.4 nm at wavelength of 450 nm. FIG. 7A shows the FL intensity of the $Tl_{0.05}Gd_{0.95}S$ nanoparticles decorated with 2-(4-(dimethylamino)styryl)-3-ethyl-benzothiazolium at different concentrations of antimony in water. The fluorescence intensity of the $Tl_{0.05}Gd_{0.95}S$ nanoparticles decorated with 2-(4-(dimethylamino)styryl)-3-ethyl-benzothiazolium was decreased as the concentration of Sb ions increased. FIG. 7B shows the dependence of the fluorescence intensity of the $Tl_{0.05}Gd_{0.95}S$ nanoparticles decorated with 2-(4-(dimethylamino)styryl)-3-ethyl-benzothiazolium on the Sb concentration in water. The FL intensity is linearly changed with the Sb ions concentration along the range 0.001 mg/L to 1000 mg/L with linear correlation factor of $R^2=0.999$. The linear relationship was fitted by the Stern-Volmer relation, which defined as $$I_o/I = 1 + K_{SV} C \qquad (1)$$

where $I_o$ and $I$ are the FL intensity of the $Tl_{0.05}Gd_{0.95}S$ nanoparticles decorated with 2-(4-(dimethylamino)styryl)-3-ethyl-benzothiazolium in the absence and presence of antimony ions, respectively. $K_{SV}$ is Stern-Volmer constant and C is the antimony ions concentration. The Stern-Volmer relation fitted well the experimental data and the $K_{SV}$ was found to be about 0.06. The detection limit (3σ) was determined and it is about 0.0001 mg/L.

Example 8

Detection of Antimony in the Presence of Foreign Ions

Figure 8:
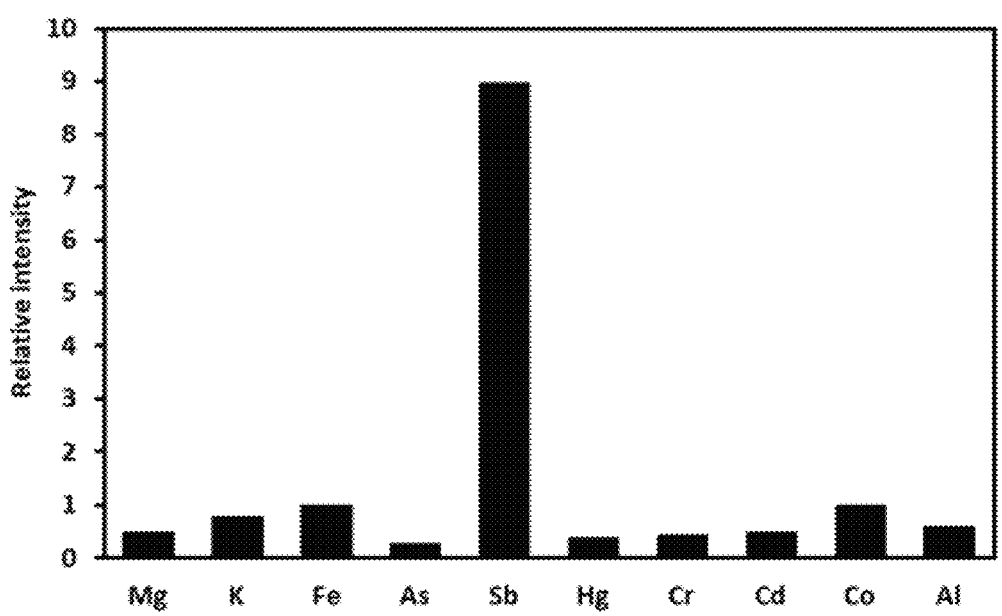
FIG. 8 illustrates the plot of the relative intensity of decorated $Tl_{0.05}Gd_{0.95}S$ nanoparticles with 2-(4-(dimethylamino)styryl)-3-ethyl-benzothiazolium for different metal ions at concentration of 100 mg/L.

Since the practical application of the fluorescence probe mainly depends on its high selectivity of the target ions, the influence of ions found abundantly in the nature on the $Tl_{0.05}Gd_{0.95}S$ nanoparticles decorated with 2-(4-(dimethylamino)styryl)-3-ethyl-benzothiazolium probe was investigated. FIG. 8 depicts the effect of some selected foreign ions on the FL intensity of the $Tl_{0.05}Gd_{0.95}S$ nanoparticles decorated with 2-(4-(dimethylamino)styryl)-3-ethyl-benzothiazolium. The $Mg^{2+}$, $K^+$, $Fe^{3+}$, $As^{3+}$, $Hg^{2+}$, $Cr^{3+}$, $Cd^{2+}$, $Co^{3+}$ and $Al^{3+}$ ions showed negligible effect compared to the $Sb^{5+}$ ions at the same concentration (100 mg/L). However, the standard deviation of 20 measurements of the FL intensity in the presence of 1 mg/L of Sb and 100 mg/L of the foreign ions was about 1.003%. The introduction of the foreign ions with different ratios (1:100, 1:1000, 1:10000 and 1:100000) showed interference less than 1.004%.

Example 9

Adsorption of Antimony on the Surface of the $Tl_{0.05}Gd_{0.95}S$ Nanoparticles Decorated with 2-(4-(Dimethylamino) Styryl)-3-Ethyl-Benzothiazolium To determine the amount of antimony adsorbed by the $Tl_{0.05}Gd_{0.95}S$ nanoparticles decorated with 2-(4-(dimethylamino)styryl)-3-ethyl-benzothiazolium probe, inductively coupled plasma mass spectroscopy was performed for the contaminated water by antimony before and after the adsorption process. Various contaminated samples were firstly prepared in waste water (contains 100 mg/L of Sb), tap water (contains 50 mg/L of Sb), well water (contains 20 mg/L of Sb), and river water (contains 10 mg/L of Sb). To each 10 ml of solution, 50 mg of the $Tl_{0.05}Gd_{0.95}S$ nanoparticles decorated with 2-(4-(dimethylamino)styryl)-3-ethyl-benzothiazolium was added and sonicated for 15 min. Then the $Tl_{0.05}Gd_{0.95}S$ nanoparticles decorated with 2-(4-(dimethylamino)styryl)-3-ethyl-benzothiazolium powder was collected by centrifuging at 14000 rpm and left to dry naturally at ambient conditions. The ICP-AES analysis for the collected $Tl_{0.05}Gd_{0.95}S$ nanoparticles decorated with 2-(4-(dimethylamino)styryl)-3-ethyl-benzothiazolium powder and the solutions after the adsorption process was performed are presented in Table 1. Table 1 shows that the antimony is adsorbed by the $Tl_{0.05}Gd_{0.95}S$ nanoparticles decorated with 2-(4-(dimethylamino)styryl)-3-ethyl-benzothiazolium. This analysis supports the interaction of antimony with the $Tl_{0.05}Gd_{0.95}S$ nanoparticles decorated with 2-(4-(dimethylamino)styryl)-3-ethyl-benzothiazolium, which allows for efficient removal of antimony from the solutions.

TABLE 1

| Sample | Amount of Sb in the sample (mg/L) | Amount of Sb adsorbed on the surface of decorated $Tl_{0.05}Gd_{0.95}S$ (mg/L) | Amount of Sb in the sample after adsorption process (mg/L) | Rate of removal (%) |
|---|---|---|---|---|
| Waste water | 100 | 99.999 | Below detection limit | 99.999 |
| Tap water | 50 | 49.999 | Below detection limit | 99.999 |
| Well water | 20 | 19.998 | Below detection limit | 99.999 |
| River water | 10 | 9.998 | Below detection limit | 99.999 |

The invention claimed is:

1. A method of detecting antimony ions in a fluid sample, comprising:
   contacting the fluid sample with a fluorescent nanocomposite to form a mixture; and
   measuring a fluorescence emission profile of the mixture to determine a presence or absence of antimony ions in the fluid sample,
   wherein a reduction in intensity of a fluorescence emissions peak associated with the fluorescent nanocomposite indicates the presence of antimony ions in the fluid sample,
   wherein the fluorescent nanocomposite comprises:
      a thallium doped gadolinium chalcogenide having formula $Tl_xGd_{1-x}Y$, wherein x is 0.01 to 0.1, and Y is selected from the group consisting of S, Se, or Te; and
      a benzothiazolium salt of formula I bound to a surface of the thallium doped gadolinium chalcogenide,

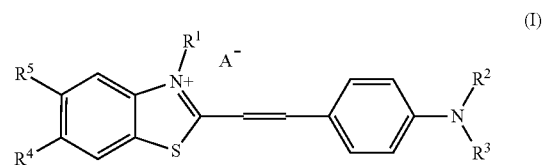

(I)

wherein:
   $R^1$ is a $C_1$-$C_4$ alkyl or an arylalkyl,
   $R^2$ and $R^3$ are independently an optionally substituted alkyl group, or wherein $R^2$ and $R^3$ together form a five or six membered ring with the nitrogen to which they are attached,
   $R^4$ and $R^5$ are independently a hydrogen or an alkyl group, and
   A is Br, I, or $ClO_4$.

2. The method of claim 1, wherein 0.5 to 10 mg of the fluorescent nanocomposite is employed per 1 mL of the fluid sample during the contacting.

3. The method of claim 1, wherein the mixture has a pH of 2 to 11 and a temperature of 10 to 70° C.

4. The method of claim 1, wherein antimony ions are present in the fluid sample, and wherein a concentration of antimony ions in the fluid sample is from 0.0001 to 1,000 mg/L.

5. The method of claim 1, wherein the fluid sample is a wastewater, a tap water, a well water, or a river water.

6. The method of claim 1, wherein the method further comprises determining a concentration of the antimony ions in the fluid sample by measuring a relative intensity of the mixture ($I_0/I$), defined as a ratio of a maximum fluorescence intensity of the fluorescent nanocomposite in a blank sample devoid of antimony ions ($I_0$) to a maximum fluorescence intensity of the mixture (I), and comparing to a calibration curve that relates antimony ion concentration to relative intensity ($I_0/I$).

7. The method of claim 1, wherein the fluid sample comprises one or more cations of potassium, magnesium, iron, arsenic, cobalt, cadmium, mercury, aluminum, and chromium, and the method is selective for detection of antimony ions, wherein only the presence of antimony ions in the mixture produces a reduction in the intensity of the fluorescence emissions peak of greater than 2%.

8. The method of claim 1, which has an antimony ion detection lower limit of 0.00001 to 0.0001 mg/L.

9. A method of removing antimony ions from a fluid sample, comprising:
    contacting the fluid sample with a fluorescent nanocomposite to form a mixture, whereby antimony ions adsorb onto the fluorescent nanocomposite to form a loaded nanocomposite; and
    separating the loaded nanocomposite from the mixture by centrifugation and/or filtration,
    wherein a concentration of antimony ions in the fluid sample after the contacting and separating is lower than an initial concentration of antimony ions in the fluid sample,
    wherein the fluorescent nanocomposite comprises:
        a thallium doped gadolinium chalcogenide having formula $Tl_xGd_{1-x}Y$, wherein x is 0.01 to 0.1, and Y is selected from the group consisting of S, Se, or Te; and
        a benzothiazolium salt of formula I bound to a surface of the thallium doped gadolinium chalcogenide,

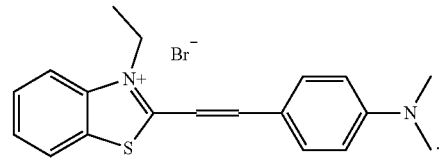

wherein:
$R^1$ is a $C_1$-$C_4$ alkyl or an arylalkyl,
$R^2$ and $R^3$ are independently an optionally substituted alkyl group, or wherein $R^2$ and $R^3$ together form a five or six membered ring with the nitrogen to which they are attached,
$R^4$ and $R^5$ are independently a hydrogen or an alkyl group, and
A is Br, I, or $ClO_4$.

* * * * *